US012788437B2

(12) United States Patent
Gerges et al.

(10) Patent No.: US 12,788,437 B2
(45) Date of Patent: Nov. 10, 2026

(54) PROTECTIVE DEVICE FOR USE DURING SURGERY

(71) Applicant: SEABAS ENTERPRISES PTY LTD, Carlingford (AU)

(72) Inventors: Bassem Gerges, Brisbane (AU); Sean Joseph Heinz, Brisbane (AU)

(73) Assignee: Seabas Enterprises Pty Ltd, Carlingford (AU)

( * ) Notice: Subject to any disclaimer, the term of this patent is extended or adjusted under 35 U.S.C. 154(b) by 0 days.

(21) Appl. No.: 18/518,198

(22) Filed: Nov. 22, 2023

(65) Prior Publication Data

US 2024/0081865 A1 Mar. 14, 2024

Related U.S. Application Data

(63) Continuation of application No. 17/452,562, filed on Oct. 27, 2021, now Pat. No. 11,857,220, which is a (Continued)

(30) Foreign Application Priority Data

Feb. 18, 2020 (AU) ................................ 2020900460

(51) Int. Cl.
*A61B 17/34* (2006.01)
*A61B 17/00* (2006.01)

(52) U.S. Cl.
CPC ...... *A61B 17/3496* (2013.01); *A61B 17/3431* (2013.01); *A61B 2017/00831* (2013.01); *A61B 2017/3484* (2013.01)

(58) Field of Classification Search
CPC ............ A61B 17/3496; A61B 17/3431; A61B 17/0493; A61B 17/0281; A61B 2017/3484; A61B 2017/00831; A61B 2090/0427; A61B 2090/0436; A61B 2090/08021; A61B 90/04
See application file for complete search history.

(56) References Cited

U.S. PATENT DOCUMENTS 5,141,515 A 8/1992 Eberbach
5,486,183 A 1/1996 Middleman
(Continued)

FOREIGN PATENT DOCUMENTS

DE 10 2012 111821 A1 6/2014
WO WO 2014/086774 A1 6/2014

OTHER PUBLICATIONS

International Search Report in PCT/AU2021/050135 issued Apr. 19, 2021.
(Continued)

*Primary Examiner* — Brigid K Byrd
(74) *Attorney, Agent, or Firm* — Knobbe, Martens, Olson & Bear, LLP

(57) ABSTRACT

A protective assembly for use during laparoscopic surgery, the assembly including: a thin membrane formed from non-toxic material, the membrane being sufficiently thin and maneuverable to be passed through a cannula of a trocar wherein the membrane includes opposed major membrane surfaces separated by thickness of the membrane, each membrane surface including rows of projections and recesses such that any two adjacently located projections are separated by a recess.

8 Claims, 15 Drawing Sheets

Related U.S. Application Data continuation of application No. PCT/AU2021/050135, filed on Feb. 18, 2021.

(56) References Cited

U.S. PATENT DOCUMENTS

| | | | | |
|---|---|---|---|---|
| 5,906,621 | A | 5/1999 | Secrest | |
| 6,652,595 | B1* | 11/2003 | Nicolo | A61F 2/0063 623/23.72 |
| 8,652,147 | B2 | 2/2014 | Hart | |
| 2003/0212461 | A1 | 11/2003 | Vadurro | |
| 2005/0165437 | A1 | 7/2005 | Takimoto | |
| 2005/0277942 | A1 | 12/2005 | Kulas | |
| 2006/0258899 | A1 | 11/2006 | Gill et al. | |
| 2007/0213734 | A1 | 9/2007 | Bleich et al. | |
| 2009/0137877 | A1 | 5/2009 | Minnelli | |
| 2010/0312253 | A1* | 12/2010 | Nevyas-Wallace | A61B 90/02 606/107 |
| 2011/0105848 | A1* | 5/2011 | Sadovsky | A61B 17/3421 600/204 |
| 2012/0029272 | A1 | 2/2012 | Shelton, IV et al. | |
| 2013/0237747 | A1 | 9/2013 | Linares | |
| 2014/0194698 | A1 | 7/2014 | Melsheimer et al. | |
| 2014/0257032 | A1* | 9/2014 | Hacker | A61B 17/06109 600/37 |
| 2014/0345629 | A1 | 11/2014 | Stockwell | |
| 2015/0148742 | A1 | 5/2015 | Satake | |
| 2015/0305734 | A1* | 10/2015 | Melsheimer | A61B 17/0293 600/233 |
| 2019/0175161 | A1 | 6/2019 | Shah et al. | |
| 2021/0153858 | A1* | 5/2021 | King | A61B 17/0218 |

OTHER PUBLICATIONS

Written Opinion of the International Searching Authoritiy in PCT/AU2021/050135 issued Apr. 19, 2021.

International Preliminary Report On Patentability in PCT/AU2021/050135 issued Jun. 10, 2020.

Extended European Search Report in corresponding European Application No. 21755688.5, dated Jul. 14, 2023.

* cited by examiner

PROTECTIVE DEVICE FOR USE DURING SURGERY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to a medical device for insertion into a patient's body and a surgical apparatus for inserting a device into a patient's body.

BACKGROUND

Minimally invasive surgery or keyhole surgery is a common surgical technique in which a surgeon makes one or more small incisions about 5 to 12 mm long in the skin through which surgical tools, lights and cameras are inserted to operate on a tissue structure in the patient's body. In contrast, in traditional or open surgery, a surgeon may make a 15 to 30 cm long incision. As a result, a patient undergoing minimally invasive surgery may suffer less post-operative pain and recover more quickly from surgery, as well as having less visible scarring than a patient undergoing open surgery.

However, minimally invasive surgery requires different hand-eye coordination skills than open surgery and requires a surgeon to view the operating space in two-dimensions on a display, limiting depth perception. In addition, the surgeon has limited haptic feedback with the tissue structure being treated and may have limited ability to retract obstructing tissue structures and expose the tissue structure to be treated due to the confined operating space. As a result, there may be a risk of inadvertent burning or perforation of tissue structures during minimally invasive surgery.

Thus, there would be an advantage if it were possible to provide a device for use during keyhole surgery that reduced or eliminated the risk of injury to a patient.

It will be clearly understood that, if a prior art publication is referred to herein, this reference does not constitute an admission that the publication forms part of the common general knowledge in the art in Australia or in any other country.

SUMMARY

The present invention is directed to a medical device for insertion into a patient's body, which may at least partially overcome at least one of the abovementioned disadvantages or provide the consumer with a useful or commercial choice.

In a first aspect, there is provided a protective assembly for use during laparoscopic surgery, the assembly comprising a thin membrane formed from non-toxic material, the membrane being sufficiently thin and maneuverable to be passed through a cannula of a trocar; a flexible connector extending from the thin membrane; and an insertable plunger to facilitate insertion of the membrane into the cannula and subsequently pass the membrane through the outlet of the cannula to allow the membrane to be spread over internal organs of the patient, the plunger comprising a shaft dimensioned to be inserted and passed through the cannula wherein a distal portion of the shaft is anchored to the flexible connector.

In another aspect, the invention provides a protective assembly for use during laparoscopic surgery, the assembly comprising: a thin membrane formed from non-toxic material, the membrane being sufficiently thin and maneuverable to be passed through a cannula of a trocar wherein the membrane comprises opposed major membrane surfaces separated by thickness of the membrane, each of the major membrane surfaces comprising rows of projections and recesses such that any two adjacently located projections are separated by a recess, wherein thickness of a portion of the membrane in between the any two adjacently located projections separated by a recess is substantially less than or equal to the average height of the projections and/or average depth of the recesses and wherein the membrane is non-porous.

In an embodiment, the flexible connector is connected to a peripheral portion of the membrane.

In an embodiment, a proximal portion of the insertable shaft comprises an enlarged head to limit inward movement of the shaft into the cannula of the trocar and prevent the shaft from falling through the trocar.

In an embodiment, the membrane comprises a plurality of fold regions to facilitate rolling or folding of the membrane to allow the membrane to pass through the cannula in a folded configuration.

In an embodiment, the membrane comprises at least two linear peripheral portions that are substantially transverse and preferably perpendicular to each other.

Preferably, the two linear peripheral portions are connected by at least one curved bridging portion to orient the linear peripheral portions in transverse configuration.

In an embodiment, a first curved bridging portion with a first arc length and a second curved bridging portion with a second arc length such that the first arc length is smaller than the second arc length to define a wing shaped membrane.

In an embodiment, width of the connector is substantially less than overall width of the membrane.

In an embodiment, length of the flexible connector is greater than the length of the cannula of the trocar.

In an embodiment, length of the flexible connector is at least twice the length of the cannula of the trocar.

In an embodiment, the membrane comprises opposed major membrane surfaces separated by thickness of the membrane, each membrane surface comprising rows of projections and recesses such that any two adjacently located projections are separated by a recess.

Preferably, each recess on one of the major membrane surfaces is shaped to form a trough and aligned with a projection on the other of the major membrane surfaces.

In an embodiment, each of the said projections on the major surfaces of the membrane extend generally in a transverse direction relative to a direction of the rows of the projections and recesses.

In an embodiment, average height of the projections is substantially equal to average depth of the recesses.

In an embodiment, thickness of the membrane portion in between the adjacently located projections and recesses is substantially less than or equal to the average height of the projections and/or average depth of the recesses.

In an embodiment, the membrane portions between adjacent projections and recesses facilitate folding or rolling of the membrane in the folded configuration.

Preferably, the connector is fused with the membrane.

Preferably, the membrane is sufficiently heat tolerant to reduce or minimize accidental damage from ablation.

In an embodiment, the flexible connector is attached to a convergent peripheral portion of the membrane such that the convergent peripheral portion converges generally in a direction towards the shaft to facilitate rolling or folding of the membrane when pulled into the cannula of the trocar during use.

In an embodiment, width of the membrane gradually broadens from a location of attachment of the connector on the membrane.

In an embodiment, length of the flexible connector is adjustable.

The present disclosure broadly provides, in another aspect, a protective device for use during surgery comprising: an expandable body adapted for at least partial insertion into a patient's body; and an inner member located at least partially within the expandable body, wherein, once expanded, the protective device is configured to protect a tissue structure within the patient's body during surgery.

The protective device may be used for any suitable type of surgery. Preferably, the protective device may be used for a surgery performed on a tissue structure in a patient's body. For instance, the surgery may be a minimally invasive procedure (such as laparoscopy, thoracoscopy, arthroscopy, hysteroscopy, appendectomy, or the like), an open surgical procedure (such as laparotomy, cholecystectomy, or the like), or any suitable combination thereof. Preferably, the protective device may be used for a surgery performed on a tissue structure in a patient's body wherein an adjacent tissue structure may need to be protected.

The protective device may be used with any suitable type of surgical apparatus. Preferably, the protective device may be used with a surgical apparatus where there may be a risk of the surgical apparatus injuring a patient or where treatment of a tissue structure with a surgical apparatus may cause injury to an adjacent tissue structure, or the like. For instance, the protective device may be used with a surgical apparatus comprising a cutting tool (such as a scalpel, a blade, scissors, a dissector, a cutter, etc.), a piercing tool (such as a needle, a cannula, a probe, etc.), a grasping tool (such as a grasper, forceps, etc.), an energy supply device (such as thermal energy, cold energy, electrical energy, etc.), a trocar, and any suitable combination thereof.

As previously stated, the protective device is adapted for at least partial insertion into a patient's body. In an embodiment of the invention, the protective device may be inserted into the patient's body such that it is at least partially received therewithin. In a preferred embodiment of the invention, the protective device may be inserted into a patient's body such that it is substantially received within the patient's body. In this instance, it is envisaged that at least a portion of the protective device may extend out of the patient's body, such as through a wound, surgical incision or the like. Preferably, the protective device may be adapted for removable insertion into a patient's body. In this instance, it is envisaged that the protective device may be temporarily inserted into the patient's body during surgery and then subsequently removed at the conclusion of the surgery (and especially prior to closing the wound or incision), rather than being permanently inserted into a patient's body.

The protective device may be of any suitable size, shape or configuration. Preferably, the size, shape and configuration of the protective device may be determined at least in part by the tissue structure to be protected and/or treated during a surgery. For instance, if a tissue structure having a large surface area is to be protected, then a larger protective device may be required in comparison to when a smaller tissue structure is to be protected. However, it will be understood that the size, shape and configuration of the protective device may vary depending on a number of factors, such as the size of the surgical incision, access port or body orifice through which the protective device is to be inserted, the type of surgical procedure to be performed, the type of surgical apparatus to be used and the tissue structure to be treated.

As previously stated, the protective device is configured to protect a tissue structure during a surgery. The protective device may protect a tissue structure by any suitable means. For instance, the protective device may at least partially enclose a tissue structure, may substantially enclose a tissue structure, may be applied as a blanket to at least partially cover a tissue structure, may be applied as a blanket substantially covering a tissue structure, may be applied as a curtain to at least partially cover a tissue structure, may be applied as a curtain substantially covering a tissue structure, and the like. Preferably however, the protective device may provide a physical, thermal, and/or electrical barrier between a surgical apparatus and a tissue structure.

In an embodiment of the invention, the protective device may be attached to a tissue structure during surgery. Preferably, the protective device may be temporarily attached to a tissue structure during surgery. In use, it is envisaged that the protective device may be temporarily attached to a tissue structure in the patient's body during surgery and then subsequently detached and removed at the conclusion of the surgery (and especially prior to closing the wound or incision). In an embodiment of the invention, the protective device may be attached to a tissue structure during surgery, such that it acts as a curtain. In this instance, it is envisaged that the protective device may cover a tissue structure. Alternatively, the protective device may protect a tissue structure by at least partially enclosing the tissue structure in the protective device. In this instance, it is envisaged that a portion of the protective device may be temporarily attached to another portion of the protective device and then subsequently detached and removed at the conclusion of the surgery. A portion of the protective device may be temporarily attached to a tissue structure and/or another portion of the protective device by any suitable technique, such as a temporary adhesive (such as a non-bonding adhesive, positioning agent, or the like), a mechanical fastener (such as stitching, staples, suture clips, suture anchors, tacks, clamps, or the like), a tether or tie, or a combination thereof. However, it will be understood that how a portion of the protective device may be attached to a tissue structure and/or another portion of the protective device may vary depending on the type and size of tissue structure to be protected, the location of the tissue structure in the patient's body, the type of material the protective device may be fabricated from, the size, shape and configuration of the protective device, and the length of surgery.

Any suitable portion of the protective device may be temporarily attached to a tissue structure and/or another portion of the protective device. For instance, the protective device may be provided with an attachment portion, wherein the attachment portion of the protective device may be configured to be attachable to a tissue structure. Any suitable attachment portion may be provided, such as a margin portion extending about at least a portion of the periphery of the protective device, one or more regions adapted to be penetrated by a mechanical fastener, one or more tabs or attachment portions, or the like. Alternatively, the protective device may be provided with one or more tethers, cords, wires or filaments, hooks or barbs, configured to attach the protective device to the tissue structure. In this instance, it is envisaged that secondary mechanical fasteners may not be required to attach the protective device to the tissue structure.

Alternatively, the protective device may be provided with one or more weighted portions, such that in use the weighted portions may reduce movement of the protective device during surgery. In this instance, it is envisaged that the weighted portions may assist in expanding the protective device from an insertion condition to a use condition, in conforming the protective device to the shape of the tissue structure, or any suitable combination thereof. The weighted portions may be of any suitable size, shape and configuration. For instance, the weighted portions may be a margin portion, a tab or attachment portion, a region adapted to receive an expansion fluid, or the like.

The protective device comprises an expandable body. The expandable body may be any suitable shape in cross-section. For instance, the expandable body may be substantially circular, oval, square, rectangular, stadium-shaped, triangular, hexagonal, or octagonal in cross-section. Preferably, however, at least one corner radius of the expandable body may be rounded. It is envisaged that in use, providing rounded corners may eliminate weak points in the expandable body, reduce the risk of the protective device tearing the surgical incision or body orifice during insertion into the patient's body, or reduce the risk of the expandable body cutting and/or perforating a tissue structure. In an embodiment of the invention, the expandable body may be substantially triangular in cross-section. For instance, the expandable body may be triangular with rounded corners, a trefoil shape, a three-lobe shape, a Reuleaux triangle, or the like.

In use, the expandable body may be moved into an insertion condition for insertion into a patient's body. It is envisaged that, in the insertion condition, the expandable body may be folded, rolled or otherwise compressed or compacted in order to allow insertion of the expandable body into a patient's body through a relatively small incision, wound or the like. In a particular embodiment, a substantially triangular expandable body (i.e., the use condition) may be moved into the insertion condition (in the form of a substantially square configuration) by folding corners of the triangular expandable body towards the center of the triangular expandable body. In this way, it is envisaged that the square expandable body may be rolled or folded to form an expandable body in an insertion condition. It is envisaged that, in the insertion condition, the outer diameter or width of the expandable body may be substantially the same along the length of the expandable body.

The expandable body may be of any suitable size. Preferably, however, the expandable body is of sufficient size to protect and/or treat a tissue structure during a surgery. In addition, it is envisaged that the expandable body is of a size that allows it to be inserted through a surgical incision, access port or body orifice. The expandable body may be of any suitable dimensions. However, it will be understood that the cross-sectional surface area of the expandable body and the thickness of the expandable body may affect the outer diameter of the expandable body in the insertion condition. For instance, a thicker expandable body may, in the insertion condition, have a greater outer diameter than a thinner expandable body when in the insertion condition. For instance, an expandable body having a relatively small cross-sectional surface area may, in the insertion condition, have a smaller outer diameter than an expandable body having a larger cross-sectional surface area.

Preferably, the outer diameter of an expandable body in the insertion condition may be less than the internal diameter of the surgical incision, access port or body orifice through which the protective device is to be inserted. In an embodiment of the invention, the outer diameter of the expandable body in the insertion condition may be less than the internal diameter of a 12 mm trocar access port, may be less than the internal diameter of a 10 mm trocar access port, may be less than the internal diameter of a 8 mm trocar access port, or may be less than the internal diameter of a 5 mm trocar access port. In a preferred embodiment of the invention, the outer diameter of the expandable body in the insertion condition (and preferably having a substantially triangular shape in cross section) may be less than the internal diameter of a 12 mm trocar access port.

The expandable body may be of any suitable thickness. Preferably however, the thickness of the expandable body is sufficient to physically, thermally and/or electrically insulate a tissue structure from a surgical apparatus. However, it will be understood that physical, thermal and/or electrical insulating properties of the expandable body may vary depending on a number of factors, such as the type of material the expandable body is fabricated from and the structure of the expandable body. It is envisaged that the thickness of the expandable body may have a direct effect on the outer diameter of the expandable body when in the insertion condition. For instance, an expandable body having a relative high thickness may need to have a smaller cross-sectional surface area in order to be inserted through a surgical incision, access port or body orifice. In an embodiment of the invention, the thickness of an expandable body may be about 0.5 to 3.0 mm, more preferably about 0.8 to 2.8 mm, even more preferably about 1.0 to 2.5 mm, and still more preferably about 1.2 to 2.3 mm. Most preferably, the thickness of the expandable body may be about 1.5 to 2.0 mm.

In an embodiment, the expandable body may be fabricated from one or more types of materials. For instance, the expandable body may be fabricated from a single material, or a single type of material. Alternatively, the expandable body may comprise different materials, or different types of materials. In an embodiment of the invention, the expandable body may comprise two or more layers of different materials. For instance, the expandable body may comprise a first layer fabricated from a first type of material and a second layer fabricated from a second type of material. Fabricating the expandable body from different types of materials may allow the expandable body to be fabricated from two or more layers having different properties, such as permeability, conductivity, resistance, or the like. In an embodiment of the invention, the expandable body may be a multi-layer structure, wherein one or more layers may be fabricated from different types of materials.

In an embodiment, the expandable body may be fabricated from one or more sheets of flexible sheet material. In an embodiment of the invention, the expandable body may be fabricated from an upper sheet member of flexible sheet material and a lower sheet member of flexible sheet material. It is envisaged that each of the upper sheet member and lower sheet member may comprise one or more layers of material. Each of the upper sheet member and the lower sheet member may comprise the same materials, the same types of materials, different materials or different types of materials. Each of the upper sheet member and the lower sheet member may comprise two or more layers of different materials. In an embodiment of the invention, the expandable body may be fabricated from a sheet of flexible sheet material, wherein the flexible sheet material may be folded so as to form an upper sheet member and a lower sheet member.

As previously stated, the protective device comprises an inner member located at least partially within the expandable body. It is envisaged that, in some embodiments of the invention, the expandable body may comprise a cavity therewithin in which the inner member is at least partially located.

In some embodiments, in which, the expandable body comprises an upper sheet member and a lower sheet member, it is envisaged that a cavity may be formed between the upper sheet member and the lower sheet member. Thus, in this embodiment of the invention, the upper sheet member and the lower sheet member may be connected to one another about at least a portion of the periphery thereof in order to form the expandable body. The upper sheet member and the lower sheet member may be connected to one another using any suitable technique, such as an adhesive, a mechanical fastener (such as stitching, staples, or the like), a heat treatment, a chemical treatment, a mechanical treatment (such as ultrasonic welding, compression, or the like), or a combination thereof.

In some embodiments, the expandable body may comprise a sleeve member. It is envisaged that the sleeve member may be open at one end only, such that a cavity is formed at the interior of the expandable body. In some embodiments, the expandable body may be fabricated as a sleeve member having a single layer, although it is envisaged that the sleeve member may comprise two or more layers.

The inner member may be of any suitable form. Preferably, however the inner member may be of sufficient mechanical properties (compressible, resilient, etc.) to allow the expandable body to be configured into a shape suitable for insertion into a patient's body, to allow the expandable body to expand to its original shape when placed in the patient's body and to allow the expandable body to be configured into a shape suitable for retraction or removal from the patient's body. For instance, the inner member may comprise a substantially solid sheet material, a sheet material comprising a plurality of cavities, a structure formed of an elongate material, a receptacle for retaining an expansion fluid therein (such as a gas, a fluid, a gel, or the like), a particulate material, and any suitable combination thereof. However, it will be understood that the type of inner member may vary depending on a number of factors, such as the type of surgical apparatus to be used and the desired properties of the expandable body. It is envisaged that in use, an inner member comprising a plurality of cavities and/or a lower surface area relative to the expandable body may be more easily compressed and/or folded than an inner member that is substantially solid. Thus, the inner member may comprise a unitary structure, or may comprise two or more discreet portions. The two or more discreet portions may be joined to one another, or in fluid communication with one another, or may be positioned spaced apart from one another. Preferably however, the inner member may be configured such that it assists in the folding of the protective device into an insertion condition. For instance, the two or more discreet portions and/or the plurality of cavities may be oriented to reduce the amount of material in the region of the fold lines.

The inner member may comprise a plurality of cavities, wherein the plurality of cavities may comprise an expansion fluid therein (such as a gas, a fluid, a gel, or the like). The expansion fluid may temporarily or permanently fill the plurality of cavities, in whole or in part. The expansion fluid may be permanently housed within the inner member or may be introduced into the inner member and/or protective device before and/or after insertion into the patient's body. However, it will be understood that whether the plurality of cavities is temporarily or permanently filled with expansion fluid and whether the plurality of cavities is filled in whole or in part, will depend on a number of factors, such as the type of material used to fabricate the inner member, the tissue structure to be treated and the type of surgical apparatus to be used. In use, it is envisaged that the plurality of cavities may be at least partially filled with expansion fluid during insertion and/or retraction of the protective device into a patient's body. The partially expanded inner member may assist in folding or rolling the expandable body into an insertion condition and provide some rigidity to the expandable body to assist in the placement and unfolding of the expandable body in the patient's body. The partially expanded inner member may assist in reducing movement of the protective device during surgery. In this instance, it is envisaged that inserting an expansion fluid into the plurality of cavities may provide a weighted portion.

In a specific embodiment, the inner member may be fabricated from a resiliently deformable material. Thus, in a preferred embodiment, the inner member may be a resiliently deformable inner member. In an embodiment of the invention, the inner member may be compressed, deflated or otherwise reduced in size, preferably under vacuum, to be configured into a shape and/or size suitable for insertion into and/or retraction or removal from the patient's body.

The inner member may be at least partially encapsulated within the cavity in the expandable body. More preferably, the inner member may be substantially encapsulated within the cavity in the expandable body. In this way, for instance, the thermal insulating capacity of the expandable body may be improved, and the expandable body may also be provided with improved water-resistance.

The inner member and the expandable body may be fastened to one another. This may be achieved using any suitable technique. However, it will be understood that the method of fastening the inner member to the expandable body may vary depending on the type of material used to fabricate the inner member and the expandable body and/or the biocompatibility, thermal or electrical insulating properties of the method of fastening the inner member and the expandable body to one another. For instance, the inner member and the expandable body may be fastened to one another using an adhesive or a mechanical fastener (such as stitching, staples, or the like), a heat treatment, a chemical treatment, a mechanical treatment (such as ultrasonic welding, compression, or the like). Preferably, however, the method of fastening the inner member and the expandable body to one another may maintain, for instance, the thermal insulating capacity and water-resistance of the expandable body.

In a preferred embodiment, the expandable body may be molded onto the inner member. In this instance, the overmolded inner member may be encapsulated by the expandable body such that the inner member may be substantially enclosed by the expandable body. In this way, the thermal insulating capacity of the expandable body may be improved, and the expandable body may have improved water-resistance.

The inner member may be provided with at least one stand-off affixed to a surface thereof. It is envisaged that during molding, at least one stand-off may contact an inner surface of a mold plate which may maintain the inner member in a centralized and substantially planar orientation. In this instance, it is understood that the at least one stand-off may not be covered by the material of the expandable body, such that a surface of the stand-off may be exposed. Alternatively, at least a portion of the expandable body may be coated or treated to provide the at least one stand-off with antimicrobial properties, water-resistance, UV-resistance, chemical-resistance, abrasion-resistance, reduced conductivity, or a combination thereof.

The at least one stand-off may of any suitable size, shape and configuration. Preferably however, the at least one stand-off may be of sufficient size, shape and configuration to maintain the inner member in a centralized orientation and maintain, for instance, the thermal insulating capacity and water-resistance of the expandable body.

The at least one stand-off may be fabricated from any suitable material or combinations of materials. Preferably however, the at least one stand-off may be fabricated from a material which is resiliently deformable and relatively tear resistant, biocompatible and sterilizable. For instance, the at least one stand-off may be fabricated from the same material as the expandable body, a different material to the expandable body, the same material as the inner member, a different material the inner member, or any suitable combination thereof. Preferably, the at least one stand-off may be fabricated from a material with resistance to one or more techniques to treat a structure. For instance, the at least one stand-off may be fabricated from a material which is cut-resistant, thermally insulating, non-conductive, radiation-impermeable, ultrasound-impermeable, gas-impermeable, fluid-impermeable, or the like. Alternatively, the at least one stand-off may be fabricated from a material which is gas-permeable, fluid-permeable, or the like. In this instance, it is envisaged, that fluid or gas applied to an outer surface of the expandable body may enter the body cavity and/or the inner member through the at least one stand-off by capillary action.

In an embodiment, the inner member may be self-expandable. For instance, the inner member may dilate from the insertion condition to a use condition when the expandable body is unrestrained. Alternatively, the inner member may be expanded with the assistance of a device such as a syringe. For instance, the syringe may be used to inject an expansion fluid (such as a gas, a fluid, a gel, or the like) into the inner member, into a cavity of the inner member, into a hollow body of the inner member, or any suitable combination thereof. Alternatively, the inner member may expand as a fluid or gas applied to an outer surface of the expandable body is absorbed through at least one stand-off. In this way, it is envisaged that the expansion of the inner member may result in the expandable body changing from the insertion condition to a use condition in which the expandable body is fully expanded. Of course, it will be understood that there may be a number of intermediate use conditions between the insertion condition and the use condition in which the expandable body is partially expanded. These intermediate use conditions may be used in situations in which, for example, there is only a limited amount of space within the patient's body for the expandable body to expand, or when only a relatively small area of tissue needs to be protected. It is envisaged that in use, a device such as a syringe may be used to remove the expansion fluid from the inner member in order to deflate the inner member so that the protective device may be removed from the patient's body. Alternatively, the expandable body may be manipulated so as to physically compress the inner member before removing the protective device from the patient's body. Alternatively, the expandable body may be connected to a vacuum device so as to compress the inner member before removing the protective device from the patient's body.

The inner member may be fabricated from any suitable material. Preferably, however, the inner member may be fabricated from a material which is relatively elastic and relatively tear resistant, biocompatible and sterilizable. For instance, the inner member may be fabricated from an extruded polymer, an expanded polymer, a foamed polymer, or combinations thereof. Preferably, the inner member may be fabricated from a relatively flexible polymer, such as, but not limited to, polycarbonate, polyethylene, polypropylene, polystyrene, polyvinyl chloride (PVC), acrylonitrile butadiene styrene, ethylene vinyl acetate (EVA), poly vinyl alcohol (PVA), ethylene propylene diene terpolymer, neoprene, nitrile, silicone, fluroelastomer, polyurethane, polyamides, nylon, polychloroprene (neoprene), polyurethane (memory foam), or the like, or any suitable combination thereof.

The inner member may be fabricated from a closed cell foam material or an open cell foam material. In an embodiment of the invention, the inner member may comprise a closed cell foam material. A closed cell foam material has an open cell content of 20% or less, 10% or less, 5% or less, and can have zero percent open cell content. In an embodiment of the invention, the inner member may be a closed cell ethylene vinyl acetate or poly vinyl alcohol foam core. In an embodiment, the inner member may be a closed cell neoprene. In an alternative embodiment of the invention, the inner member may comprise an open cell foam material. An open cell foam material has an open cell content of 50% or more, 60% or more, 70% or more, 80% or more, 90% or more and can have 100% open cell content. In an embodiment of the invention, the inner member may be an open cell ethylene vinyl acetate or poly vinyl alcohol foam core. In an embodiment of the invention, the inner member may be a memory foam. In an embodiment of the invention, the inner member may be an open cell neoprene. It is envisaged that a user may expand an open cell foam material by injecting an expansion fluid into the open cell foam material. For instance, the expansion fluid may be injected into an expansion portion associated with the open cell foam material or alternatively, the expansion fluid may be injected directly into the open cell foam material.

The inner member may be fabricated from a network of elongate material. Any suitable type of elongate material may be used. Preferably, however, the elongate material may be expandable or self-expandable. For instance, the elongate material may comprise flexible tubing, pneumatic tubing, balloon tubing, lumen tubing, an expandable sleeve, a stent component, or the like. In this instance, it is envisaged that a user may expand the network of elongate material by injecting an expansion fluid into an opening in the network of elongate material. For instance, the expansion fluid may be injected into an expansion portion associated with the network of elongate material or alternatively, the expansion fluid may be injected directly into the network of elongate material.

Any suitable expansion fluid may be used. For instance, the expansion fluid may be a gas, a fluid, a gel, or any suitable combination thereof. Preferably, however, the expansion fluid may be non-flammable and non-toxic. In an embodiment where the expansion fluid may be a fluid, a gel, or a suitable combination thereof, it is envisaged that by injecting the expansion fluid into the inner member of the protective device, it may add weight to the protective device and reduce movement of the protective device within the patient's body.

The expandable body may be fabricated from any suitable material or combinations of materials. Preferably, however, the expandable body may be fabricated from a material which is relatively elastic and relatively tear resistant, biocompatible and sterilizable. Preferably, the expandable body may be fabricated from a material which is non-adherent. Preferably, the expandable body may be fabricated from a material with resistance to one or more techniques to treat a tissue structure. For instance, the expandable body may be fabricated from a material which is cut-resistant, thermally insulating, non-conductive, radiation-impermeable, ultrasound-impermeable, gas-impermeable, fluid-impermeable, or the like.

Alternatively, the expandable body may be fabricated from a material which focuses or directs one or more techniques to treat a tissue structure. For instance, the expandable body may be fabricated from a material which is cut-resistant, thermally conductive, electrically-conductive, radiation-permeable, ultrasound-permeable, gas-permeable, fluid-permeable, or the like. In this instance, it is envisaged that the expandable body may be used to focus treatment on the tissue structure covered by the protective device.

The expandable body may be fabricated from any suitable material. Preferably, however the expandable body may be fabricated from a flexible material. For instance, the expandable body may be fabricated from a polymer such as, but not limited to, polyvinylchloride, silicone, Teflon PTFE, nitrile, thermoplastic elastomers, thermoplastic urethanes, polyethylene, polyurethane, or the like, or any suitable combination thereof. Preferably, the expandable body may be fabricated from a silicone. However, it will be understood that the type of material used may vary depending on a number of factors, such as the size of the surgical incision, access port or body orifice through which the protective device is to be inserted, the type of surgical procedure to be performed, the type of surgical apparatus to be used and the tissue structure to be treated.

In an embodiment, one or more layers of the expandable body may be fabricated from a thermally insulating, non-conductive material. Preferably, one or more layers of the expandable body may be fabricated from a thermally insulating, non-conductive material which is resistant to energy and/or contact burns from a surgical tool. In this instance, it is envisaged that the expandable body may reduce or minimize the risk of burns or damage to the tissue structure to be protected and insulates the tissue structure from energy leaks.

In an embodiment, the protective device may comprise a retention member. Any suitable retention member may be used. Preferably, however, the retention member is flexible, sterilizable, and non-conductive. For instance, the retention member may be a suture material, a cord, a cable, a guidewire, a tether, or the like. Preferably, however, the retention member is of sufficient size and strength to retain connection with the protective device during surgery and withdraw the protective device from the patient's body. It is envisaged that the purpose of the retention member may be both to ensure that a user may be able to use the retention member to withdraw the device from the patient's body, and also to prevent the need to create a larger incision to retrieve the device from the patient's body.

The retention member may be fabricated from natural materials, synthetic materials, or a combination thereof. Any suitable material may be used, such as natural materials (including silk, catgut, cotton, flax, hemp, or the like), a metal or metal alloys (including metal wire, rope or the like), polymers such as nylon, polypropylene, polyethylene (including HDPE, PET and so on), polyamideimide (including glass-filled polyamideimide), polyphenylene sulphide, polyetheretherketone, polyetherimide or the like, or any suitable combination thereof. In some embodiments of the invention, the retention member may be coated or treated to provide the substrate with antimicrobial properties, water-resistance, UV-resistance, chemical-resistance, abrasion-resistance, reduced conductivity, or a combination thereof.

The retention member may be provided in the form of a monofilament, or may comprise a plurality of strands. In some embodiments, the retention member may be fabricated from metal and coated with or surrounded by a polymeric material (such as a polymeric sleeve or tube surrounding a metal wire, cable, or the like) or set in a bio-degradable sleeve deemed appropriate for the environment.

The retention member may be of any suitable length. Preferably, however the retention member may be of sufficient length such that after the protective device is released into the patient's body and placed on the tissue structure to be protected, at least a portion of the retention member may be outside the patient's body at all times. In this way, the protective device may be able to be retrieved after a surgery, which may not be the case if the retention member is not of sufficient length. Thus, the retention member is preferably relatively long. However, it will be understood, that if the retention member is too long, there may be a risk of the retention member becoming caught on a tissue structure or another surgical instrument in the patient's body. Therefore, more preferably, the excess length of the retention member may be housed in or attached to a surgical apparatus used to place the protective device in a patient's body.

The retention member may be configured for attachment to the expandable body. The retention member may be attached to the expandable body by any suitable means. For instance, the retention member may be provided with a connection member, may be integrally formed with the expandable body, may be directly attached to the expandable body (such as by passing an end of the retention member through an aperture in the expandable body), or any suitable combination thereof. Preferably however, the retention member provides the user with the ability to retain connection with the protective device when inserted in a patient's body.

The retention member may be provided with a connection member to attach the retention member to the expandable body. Any connection member may be used. Preferably however, the connection member facilitates the attachment of the retention member to the expandable body. For instance, the retention member may be provided with a connection member such as an adhesive or a mechanical fastener (such as a screw, a staple, a pin, an anchor, an arrow, or the like).

Alternatively, the retention member may be manipulated to form a connection member, such as by tying a knot, or by applying a heat or chemical treatment which may melt an end of the retention member to the standing part of the retention member. However, it will be understood that the type and number of connection members used may vary depending on the type of retention member used and the type of expandable body.

The protective device may comprise an expansion portion. The expansion portion may be of any suitable type. Preferably, however, the expansion portion enables the injection and/or extraction of an expansion fluid into an expandable body in order to change the expandable body from the insertion condition to a use condition.

In a preferred embodiment, the expansion portion includes one or more valves. Any suitable valves may be provided, such as one or more one-way (non-return) valves or the like. One-way valves may be used to prevent the unwanted or accidental removal of expansion fluid from the expandable body. In these embodiments of the invention, it is envisaged that the expansion portion may comprise one or more additional valves adapted to allow expansion fluid to leave the expandable body to either make adjustments to the expansion of the expandable body, or to remove the expansion fluid from the expandable body, for instance at the conclusion of the surgery.

In other embodiments, the expansion portion may include one or more two-way valves, luer activated valves, or the like. The expansion portion may be configured to expand the inner member and/or the expandable body.

In a preferred embodiment, the one or more valves in the expansion portion may comprise the only points in the protective device through which fluid may enter or exit the device.

A source of expansion fluid may be connected to the expansion portion in order to inject an expansion fluid into the expandable body. The source of fluid may be any suitable type. For instance, the source of fluid may comprise a gas cylinder, reservoir, IV bag, syringe or the like, or any combination thereof. In embodiments of the invention in which the source of expansion fluid comprises a syringe, it is envisaged that by injecting the expansion fluid into the expandable body, the expandable body may expand, enabling it to be used to protect a tissue structure during a surgery. A syringe may be connected to the expansion portion in order to extract an expansion fluid from the expandable body. In this instance, it is envisaged that by extracting the expansion fluid from the expandable body, the expandable body may deflate, enabling it to be removed from the patient's body.

In yet another aspect, the disclosure provides a surgical apparatus, the surgical apparatus comprising: a protective device comprising: an expandable body, wherein the expandable body comprises at least one inner member located within the expandable body, wherein the at least one inner member is expandable; wherein the protective device is configured to protect a tissue structure within the patient's body during surgery; and a surgical instrument configured to receive at least a portion of the protective device, wherein the surgical instrument is configured to release the protective device into the patient's body during surgery.

Preferably, the protective device is the protective device of the first aspect of the invention.

The surgical apparatus comprises a surgical instrument configured to receive at least a portion of a protective device. The surgical apparatus may be disposable. In this instance, it is envisaged that the surgical apparatus may be provided to a user as a sterilized system comprising a protective device already inserted into the surgical instrument and ready for use. Alternatively, the surgical apparatus may be re-usable. In this instance, it is envisaged that the surgical instrument may be re-usable and sterilizable and the protective device may be single use only. Alternatively, both the surgical instrument and the protective device may be reusable and sterilizable.

The surgical instrument may be of any suitable configuration. In an embodiment of the invention, the surgical instrument may comprise an end effector connected to a laparoscopic tool, wherein the end effector is configured to receive at least a portion of the protective device therein. In an alternative embodiment of the invention, the surgical instrument may comprise a housing portion, the housing portion configured to receive at least a portion of the protective device therein. Preferably, however, the configuration of the surgical instrument facilitates the insertion of the protective device through a surgical incision, access port or body orifice.

In an embodiment, the surgical instrument comprises an end effector. The end effector may be connected to a surgical instrument. In an embodiment of the invention, the end effector may be removably connected to a surgical instrument. In this instance, it is envisaged that the end effector may be removably connected to the surgical instrument so as to facilitate the replacement of the end effector. Preferably, the end effector may be operable by manipulation of the surgical instrument. Thus, in a preferred embodiment, the surgical instrument may comprise a handle, an elongate barrel and an end effector.

The end effector may be of any suitable size, shape or configuration. Preferably, however the end effector is of a sufficient size, shape and configuration to be able to be inserted through a surgical incision, access port or body orifice and receive at least a portion of the protective device therein. The end effector may be of any suitable type. Preferably, however, the end effector is configured to receive at least a portion of the protective device. For instance, the end effector may comprise a longitudinally extending interior compartment located at or towards an end of the surgical instrument. Alternatively, the end effector may comprise a detachable end member configured for operable connection to an end of a surgical instrument. In this instance, it is envisaged that a detachable end member may be of similar cross-sectional dimensions to the surgical instrument. In use, it is envisaged that the end effector may comprise an opening such that the protective device may be deployed from the surgical instrument into the patient's body through the opening. The opening may be of any suitable configuration. For instance, the opening may be longitudinally extending at least partially along the length of the end effector, may extend at least partially circumferentially about the end effector, may be located at an end of the end effector, or any suitable combination thereof.

In an embodiment, the surgical instrument may comprise a housing portion, the housing portion configured to receive at least a portion of the protective device therein. The housing portion may be of any suitable size, shape or configuration. Preferably, the housing portion may be an elongate housing portion. Preferably, however the housing portion is of sufficient size, shape and configuration to be able to be inserted through a surgical incision, access port or body orifice and receive at least a portion of the protective device therein. Preferably, the protective device may be in the insertion (i.e., unexpanded) condition when located in the housing portion.

The housing portion may be configured to receive the protective device by any suitable means. The housing portion comprises a first end and an opposed second end and a bore extending at least part way through the housing portion from the first end to the second end. Preferably, the bore may extend all of the way through the housing portion from the first end to the second end. Thus, it is envisaged that the bore may comprise a pair of open ends, or one open end and one closed end. The bore may be substantially linear or may have a curved or tortuous path. The bore may be of any suitable length and any suitable diameter. The diameter of the bore may be substantially constant along its length or may vary along its length. For instance, the bore may taper along at least a portion of its length, may include a neck, or similar narrowing portion, and the like. In use, it is envisaged that the protective device may be deployed through the second end of the housing portion.

The housing portion may also include at least one projection extending outwardly therefrom. Any suitable projection may be provided, although in a preferred embodiment of the invention, the projection may comprise a flange. In an embodiment of the invention, at least one flange may be located on an external surface of the housing portion. Preferably, the flange may be located on an external surface of the housing portion towards the first end of the housing portion or located at the first end of the housing portion. It is envisaged that a flange located on an external surface of the housing portion may preclude the housing portion from passing into or through a surgical incision, access port or body orifice and into the patient's body. Thus, it is envisaged that the flange may extend outwardly from the external surface of the housing portion such that the diameter of the housing portion (including the flange) is at least equal to the diameter of the surgical incision, access port or body orifice. The flange may extend at least partially about the circumference of the housing portion. Alternatively, the flange may extend about substantially the entire circumference of the housing portion. Thus, in some embodiments, the flange may be an annular flange.

The surgical instrument may be configured to release the protective device into the patient's body. The mechanism to release the protective device into the patient's body may be of any suitable type. In an embodiment of the invention in which the surgical instrument comprises an end effector, the end effector may be actuated by manipulation of an actuating portion to release the protective device. In an alternative embodiment of the invention in which the surgical instrument comprises a housing portion, the housing portion may be configured to receive a plunger therein and wherein movement of the plunger within and relative to the housing portion releases the protective device.

In an embodiment, the surgical instrument may comprise an end effector, wherein the end effector may be actuated by manipulation of an actuating portion. In this way, it is envisaged that actuating the end effector may release the protective device into the patient's body. Any suitable actuating portion may be used. Preferably, however the actuating portion may move the end effector between an open configuration and a closed configuration. For instance, the actuating portion may be a trigger device, a ratchet device, a spring biased piston instrument, a cable-tensioned device, or the like. The actuating portion may be associated with the surgical instrument in any suitable manner. For instance, the actuating portion may be part of the surgical instrument or may be an independently operated surgical instrument. In use, it is envisaged that moving the end effector to an open configuration may allow the protective device to be removed from the end effector. The protective device may be removed from the end effector manually by a user or a robotic device, may fall out of the end effector under gravity, may be ejected from the end effector using a mechanism associated with the surgical instrument, and any suitable combination thereof.

In an embodiment, the surgical instrument may comprise a housing portion, wherein the housing portion may be configured to receive a plunger therein. In this way, it is envisaged that substantially linear movement of the plunger within the housing portion may release the protective device through the second end of the housing portion and into the patient's body. More specifically, it is envisaged that a portion of the plunger may contact or engage with a portion of the protective device within the housing portion. In this embodiment, movement of the plunger relative to the housing portion may result in a corresponding movement of the protective device relative to the housing portion. Preferably, movement of the plunger relative to the housing portion moves (for instance, by pushing) the protective device towards and out of an open end of the housing portion.

Preferably, however the plunger is of sufficient size, shape and configuration to be received within the bore of the housing portion and to move the protective device within the housing portion. The plunger may be entirely received within the bore of the housing portion. Alternatively, a portion of the plunger may protrude from the bore of the housing portion. Preferably, the cross-sectional shape of the plunger may be substantially identical to the cross-sectional shape of the bore of the housing portion, such that the plunger may be received within the bore.

The plunger may be of any suitable size, shape or configuration. For instance, the plunger may be substantially solid, may be at least partially hollow, may comprise a shaft having a plurality of longitudinal and radially extending vanes, may comprise a shaft having a plurality of transversely extending ribs along the length of the shaft, and any suitable combination thereof. Preferably, the plunger may be an elongate plunger comprising a first end and an opposed second end. In an embodiment of the invention, the plunger comprises a recessed portion, and preferably an elongate recessed portion (such as a channel) extending longitudinally along at least a portion of the length of the plunger between the first end and the second end thereof. The recessed portion may be of any suitable size, shape and configuration. Preferably however, the recessed portion is of sufficient size and configuration to receive at least a portion of the retention member of the protective device therewithin. Alternatively, the plunger may comprise a bore extending at least partially through the plunger between the first end and the second end. In use, it is envisaged that the retention member of the protective device may pass through the bore of the plunger.

As previously stated, the plunger may comprise a first end and an opposed second end. It is envisaged that, in use, the second end may contact the protective device to cause movement of the protective device relative to the housing portion. In this embodiment of the invention, it is envisaged a force may be applied to the first end of the plunger in order to actuate movement of the plunger relative to the housing portion. In some embodiments of the invention, the first end may be provided with a contact portion against which the force may be applied. The force may be applied by a user, a robotic device or the like.

The plunger may also include at least one projection extending outwardly therefrom. Any suitable projection may be provided, although in a preferred embodiment of the invention, the projection may comprise a flange. In an embodiment of the invention, at least one flange may be located on an external surface of the plunger. Preferably, the flange may be located on an external surface of the plunger towards the first end of the plunger or located at the first end of the plunger. It is envisaged that a flange located on an external surface of the plunger may preclude the plunger from passing fully into the bore of the housing portion. Thus, it is envisaged that the flange may extend outwardly from the external surface of the plunger such that the diameter of the plunger (including the flange) is at least equal to the diameter of the housing portion. The flange may extend at least partially about the circumference of the plunger. In an embodiment of the invention, the plunger may comprise two flanges provided on opposite sides of the plunger. Thus, in some embodiments of the invention, the two flanges may facilitate the removal of an anchoring device from the flange of the plunger. Alternatively, the flange may extend about substantially the entire circumference of the plunger. Thus, in some embodiments of the invention, the flange may be an annular flange. In an embodiment of the invention, the flange may be provided with a recessed portion substantially aligned with a recessed portion in the plunger.

In an embodiment, at least a portion of the flange of the plunger may contact at least a portion of the flange of the housing portion when the plunger is fully received within the bore of the housing portion. In an embodiment of the invention, at least a portion of the flange of the plunger may be at least partially received within at least a portion of the flange of the housing portion when the plunger is fully received within the bore of the housing portion. In this instance, it is envisaged that the flange of the plunger may abut the flange of the housing portion when the plunger is fully received within the bore of the housing portion and may provide a seal to prevent insufflation gas from escaping the patient's body. The plunger may be integrated with the housing portion or may be provided as a separate structure.

The surgical instrument may be provided with an anchoring portion. The anchoring portion may be of any suitable size, shape or configuration. Preferably, however, the anchoring portion may be of sufficient mechanical properties to retain at least a portion of the retention member of the protective device in connection with the surgical instrument after the protective device has been released into the patient's body. The anchoring portion may be integrated with the surgical instrument and configured to receive at least a portion of the retention member. For instance, the anchoring portion may be a projection, an aperture, a bore, a slot, a mechanical fastener (such as a clip, a set screw, or the like), or any suitable combination thereof. Alternatively, the anchoring portion may be provided as a separate structure which may be configured to temporarily connect the retention member to a portion of the surgical instrument. In this instance, it is envisaged that at least a portion of the anchoring portion may be at least partially received within at least a portion of the flange of the plunger. For instance, the anchoring portion may be substantially circular in cross-section and configured to be received within at least a portion of the flange of the plunger. For instance, the anchoring portion may comprise an enlarged region of the retention member that acts as a stop member. The enlarged region of the retention member may be sized or shaped to substantially preclude movement of the enlarged region relative to the flange of the plunger.

The anchoring portion may be configured for attachment to the retention member. For instance, the anchoring portion may be provided with a connection member that facilitates the attachment of the retention member to the surgical instrument. Alternatively, the retention member may be directly attached to the anchoring portion (such as by passing an end or loop of the retention member through an aperture in the anchoring portion or by passing an end or loop of the retention member about a region of the anchoring portion), or any suitable combination thereof. In an embodiment of the invention, the anchoring portion may be configured for removable attachment to the retention member. For instance, the anchoring portion may retain the retention member in frictional engagement resulting from the pressure fit of the retention member within the anchoring portion. For instance, the anchoring portion may be provided with a recessed portion, notch, slot, or the like configured to receive at least a portion of the retention member in frictional engagement. Thus, in use, it is envisaged, the retention member may be removed from the anchoring portion and/or the surgical apparatus after the protective device is deployed in the patient's body. Alternatively, the retention member may be attached to the anchoring portion using an adhesive, heat treatment, chemical treatment, or any suitable combination thereof. Preferably however, the retention member provides the user with the ability to retain connection with the protective device when the protective device is inserted into a patient's body.

The protective device may be secured with a sleeve. It is envisaged that the sleeve may be configured to maintain the expandable body of the protective device in the insertion condition during insertion of the protective device into the patient's body. The sleeve may be removed from the protective device manually by a user or a robotic device or may be removed from the protective device as it is ejected from the end effector. Alternatively, the protective device may be secured with at least a portion of the retention member. In this instance, it is envisaged that when the protective device is released into the patient's body, the retention member may unwrap from the protective device enabling the expandable body to expand into a use condition.

The present disclosure provides a number of advantages over the prior art. For instance, the present disclosure provides a protective device for use during keyhole surgery that reduces or eliminates the risk of injury to a patient. In addition, the present disclosure is adapted for removable insertion into a patient's body and is configured such that connection is maintained with the protective device throughout the surgery so that the protective device cannot be inadvertently left in the patient's body.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DESCRIPTION

Figure 1:
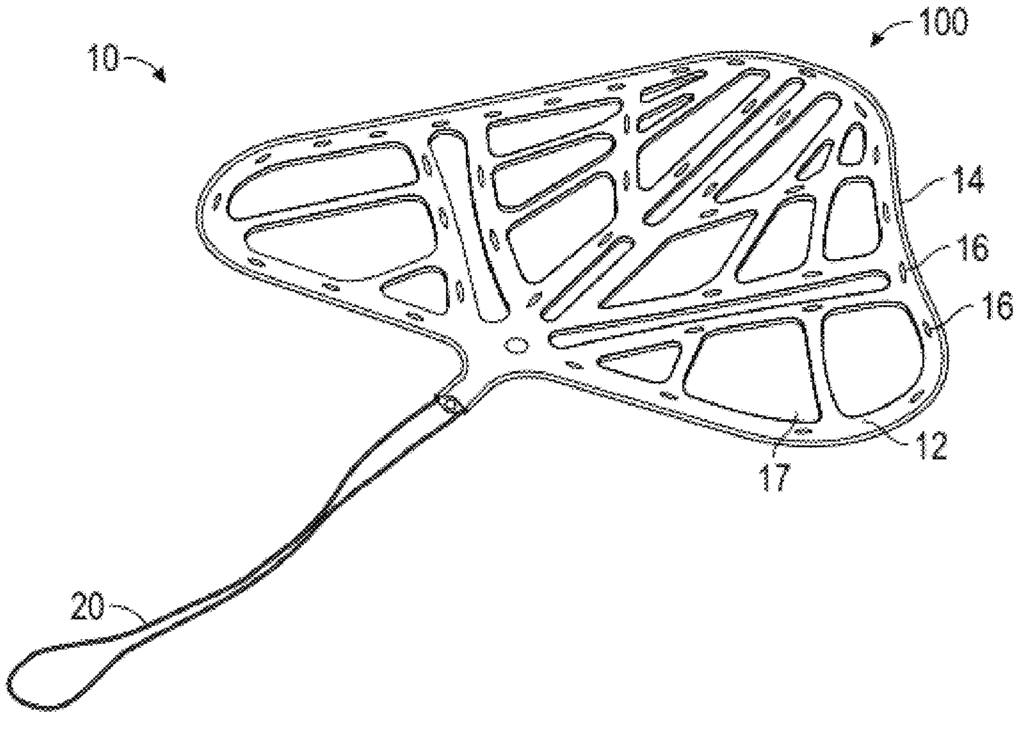
FIG. 1 illustrates a top perspective view of a protective device in a use condition according to an embodiment.

FIG. 1, a protective device for use during surgery according to an embodiment is illustrated. Protective device 100 comprises an expandable body 10 and an inner member 12 located at least partially within expandable body 10. Expandable body 10 comprises a layer 14 of silicone over-molded onto inner member 12 in the form of PVA or EVA open or closed cell foam. In use, it is envisaged that silicone layer 14 may provide resistance to energy and/or contact burns from a surgical tool and the inner member 12 may thermally insulate the tissue to be protected. Inner member 12 comprises at least one stand-off 16 which assists in maintaining inner member 12 in a centralized and substantially planar orientation during over-molding. Inner member 12 comprises a plurality of cavities 17 oriented about the fold lines (not shown) which may assist in compressing or folding the protective device into an insertion condition.

It is envisaged that in an embodiment comprising a closed cell foam inner member, such as a memory foam, the expandable body 10 expands as the inner member 12 self-inflates. It is envisaged that, in an embodiment comprising an open cell foam inner member, inner member 12 may be expanded by contacting at least one stand-off 16 with an expansion fluid or by injecting an expansion fluid directly into the inner member 12.

Protective device 100 further comprises a retention member 20 associated with expandable body 10. In use, retention member 20 may be used to by a user to withdraw protective device 100 from a patient's body.

Figure 2:
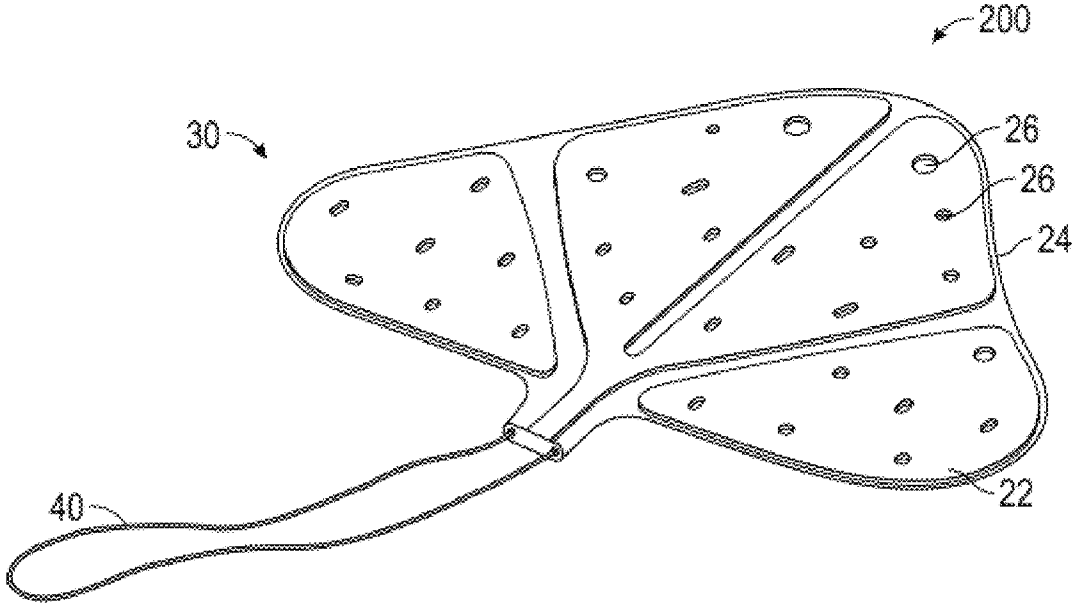
FIG. 2 illustrates a top perspective view of a protective device in a use condition according to an embodiment.

In FIG. 2, a protective device for use during surgery according to an embodiment is illustrated. Protective device 200 comprises an expandable body 30 and an inner member 22 located at least partially within expandable body 30. Expandable body 30 comprises a layer 24 of silicone over-molded onto inner member 22 in the form of PVA or EVA open cell foam. In use, it is envisaged that the silicone layer may provide resistance to energy and/or contact burns from a surgical tool and the open cell foam layer may thermally insulate the tissue to be protected.

Inner member 22 comprises at least one stand-off 26 which assists in maintaining inner member 22 in a centralized and substantially planar orientation during over-molding. Inner member 22 comprises one or more portions oriented about the fold lines (not shown) of protective device 200. In this way, the amount of material in the region of the fold lines is reduced which assists in folding the protective device into an insertion condition.

In use, it is envisaged that inner member 22 may need to be compressed under vacuum to assist in folding the protective device into an insertion condition or to deflate the inner member such that the protective device may be removed from the patient's body. In use, it is envisaged that in an embodiment comprising an open cell inner member, that inner member 22 may be expanded by contacting at least one stand-off 26 with an expansion fluid or by injecting an expansion fluid directly into the inner member 22. It is envisaged that in an embodiment comprising a closed cell foam inner member, such as a memory foam, the expandable body 30 expands as the inner member 22 self-inflates.

Protective device 200 further comprises a retention member 40 associated with expandable body 30. In use, retention member 40 may be used to by a user to withdraw protective device 200 from a patient's body.

Figure 3:
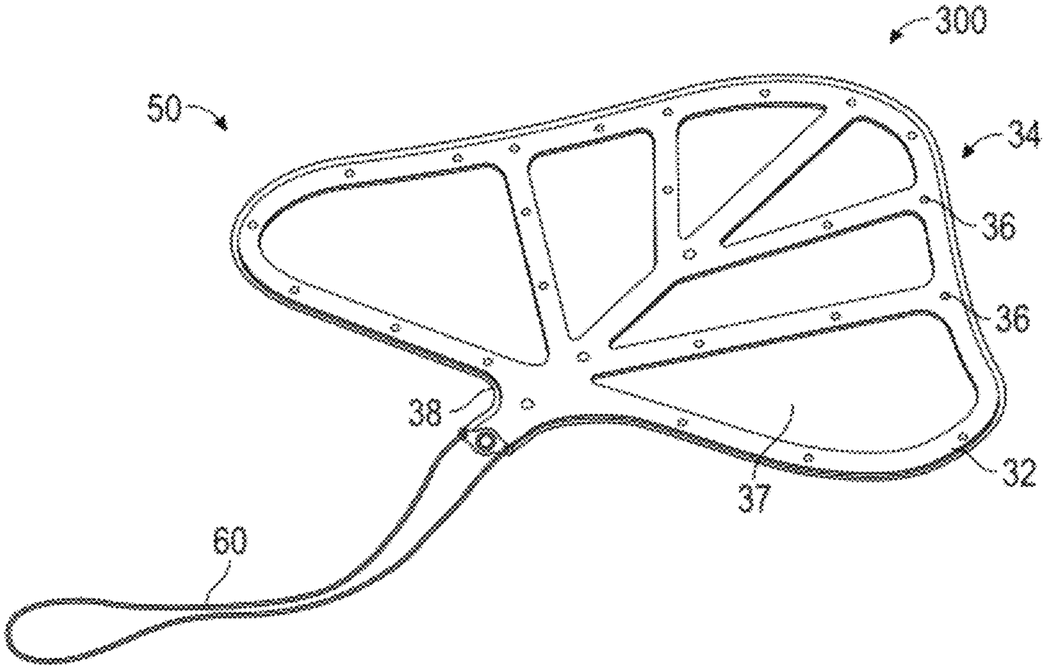
FIG. 3 illustrates a top perspective view of a protective device in a use condition according to an embodiment.

In FIG. 3, a protective device for use during surgery according to an embodiment of the invention is illustrated. Protective device 300 comprises an expandable body 50, an inner member 32 located at least partially within expandable body 50, and an expansion portion 38 associated with expandable body 50 and configured to facilitate expansion thereof. Expandable body 50 comprises a layer 34 of silicone over-molded onto inner member 32 in the form of an elongate material such as pneumatic tubing. In use, it is envisaged that silicone layer 34 may provide resistance to energy and/or contact burns from a surgical tool and the air pockets 37 between the elongate material 32 may thermally insulate the tissue to be protected. Inner member 32 comprises at least one stand-off 36 which assists in maintaining inner member 32 in a centralized and substantially planar orientation during over-molding. Inner member 32 comprises a plurality of elongate material oriented along the fold lines (not shown) which when deflated may assist in compressing or folding the protective device into an insertion condition.

In use, it is envisaged that a user may inject an expansion fluid into expansion portion 38, expanding the pneumatic tubing 32 and subsequently, expandable body 50. Alternatively, a user may expand the expandable body 50 by contacting at least one stand-off 36 with an expansion fluid or by injecting an expansion fluid directly into the at least one stand-off 36.

Figure 4:
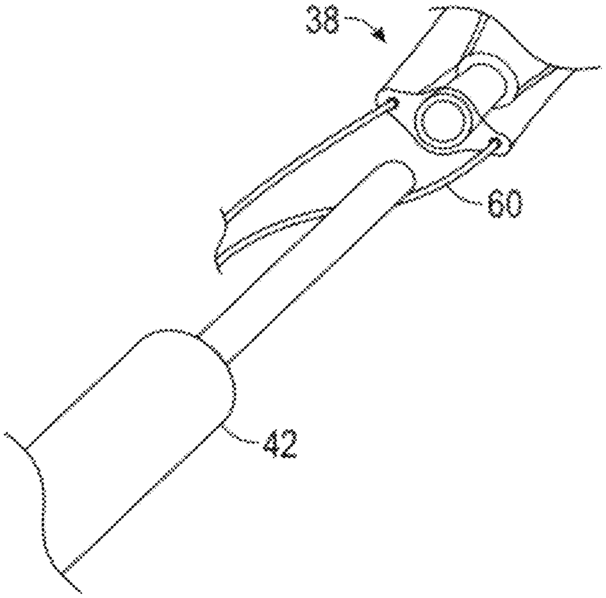
FIG. 4 illustrates an expansion portion of a protective device as illustrated in FIG. 3.

Protective device 300 further comprises a retention member 60 associated with expandable body 50. In use, retention member 60 may be used to by a user to withdraw protective device 300 from a patient's body. In FIG. 4, an expansion portion of a protective device is illustrated. A syringe 42 is used to inject an expansion fluid into expansion portion 38 of protective device 300.

Figure 5A:
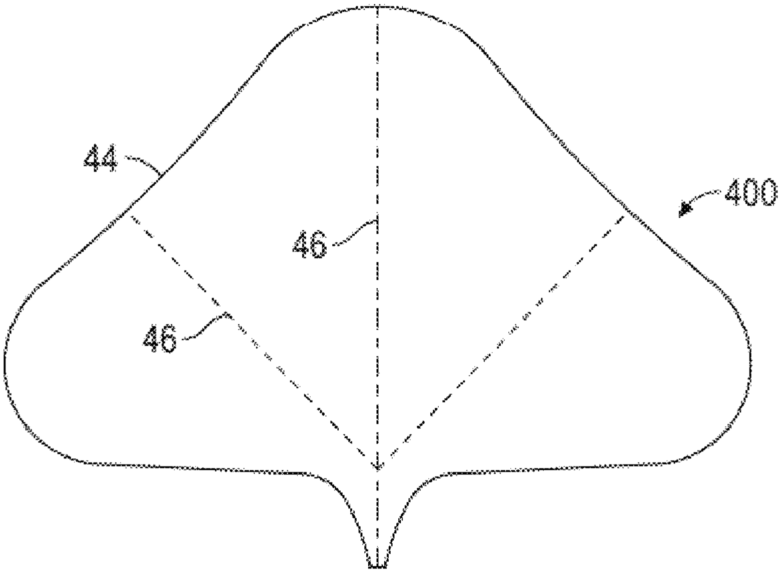
FIG. 5A illustrates a top view of a protective device in a use condition according to an embodiment.
Figure 5B:
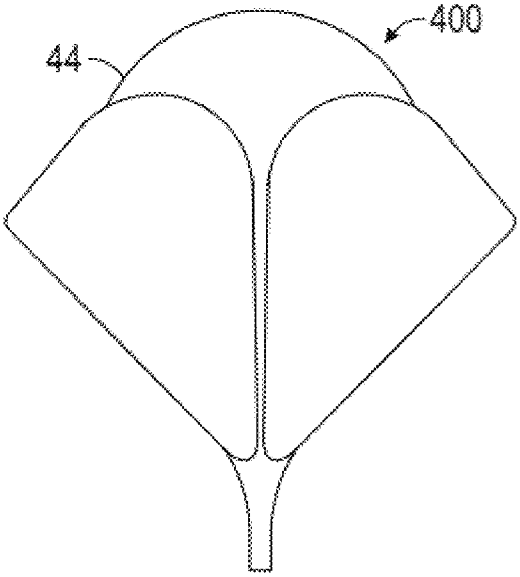
FIG. 5B illustrates a top view of a partly folded protective device according to an embodiment.
Figure 5C:
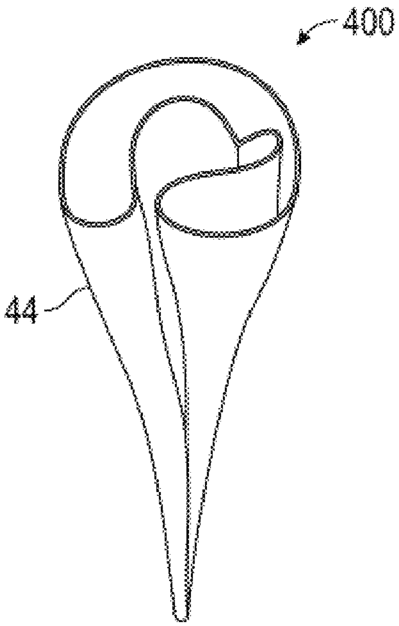
FIG. 5C illustrates a top view of a protective device in insertion condition according to an embodiment.

In FIG. 5A to 5C, a protective device 400 comprising an expandable body 44 is illustrated. In use, expandable body 44 in a fully expanded condition (FIG. 5A) is deflated and then folded along fold lines 46 to form a partly folded protective device in a substantially square configuration (FIG. 5B) and rolled into an insertion condition (FIG. 5C).

Figure 6:
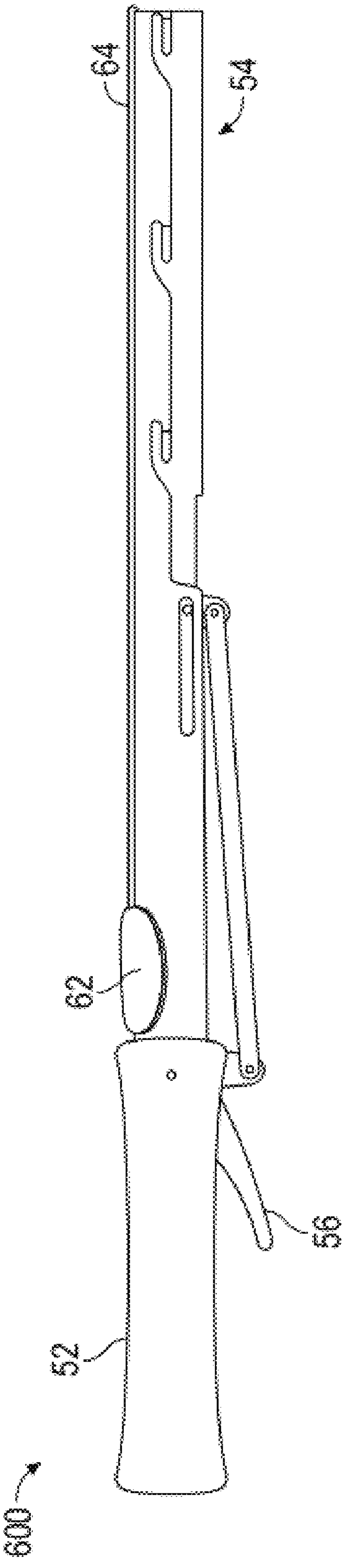
FIG. 6 illustrates a side view of a surgical apparatus according to an embodiment of the invention in a closed condition.
Figure 7:
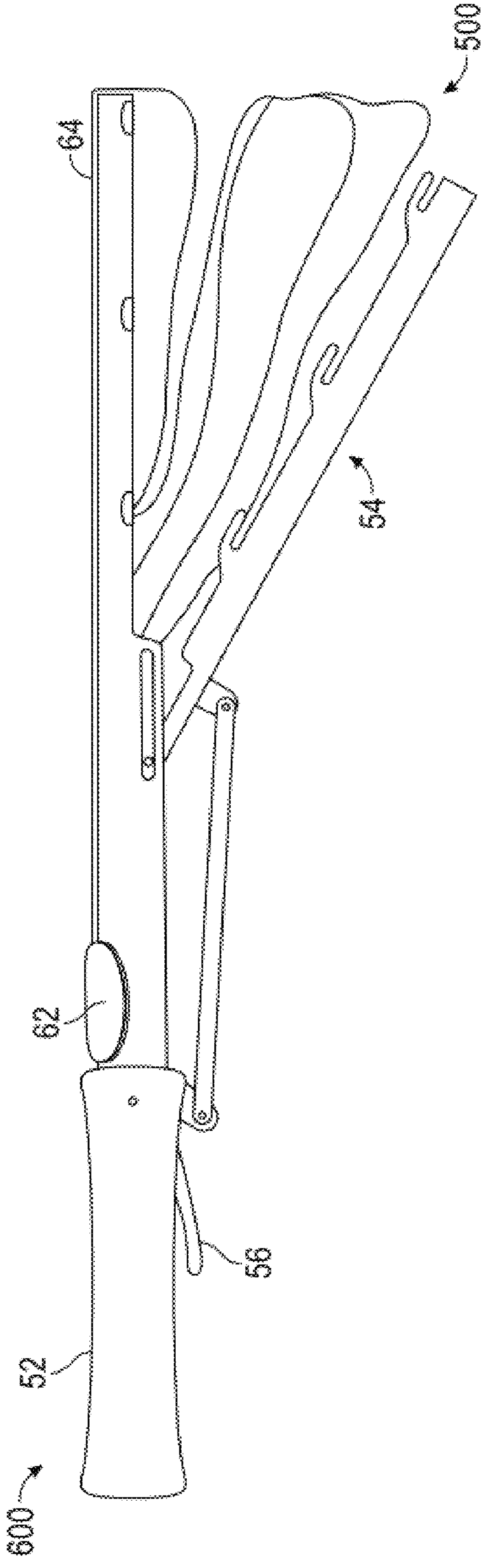
FIG. 7 illustrates a side view of a surgical apparatus according to an embodiment of the invention in an open condition.

In FIGS. 6 and 7, a surgical apparatus comprising a surgical instrument and a protective device for insertion into a patient's body is illustrated. Surgical instrument 600 comprises an end effector 54 configured to receive at least a portion of protective device 500 therein. End effector 54 is actuated by an actuating portion 56 in the form of a trigger device attached to handle 52 of the surgical instrument to move end effector 54 between a closed configuration and an open configuration. It is envisaged that in use, moving end effector 54 to an open configuration may allow protective device 500 to be inserted into or removed from end effector 54. End effector 54 comprises anchoring portion 65 configured to retain at least a portion of retention member 64 of protective device 500 in connection with surgical instrument 600.

Figure 8:
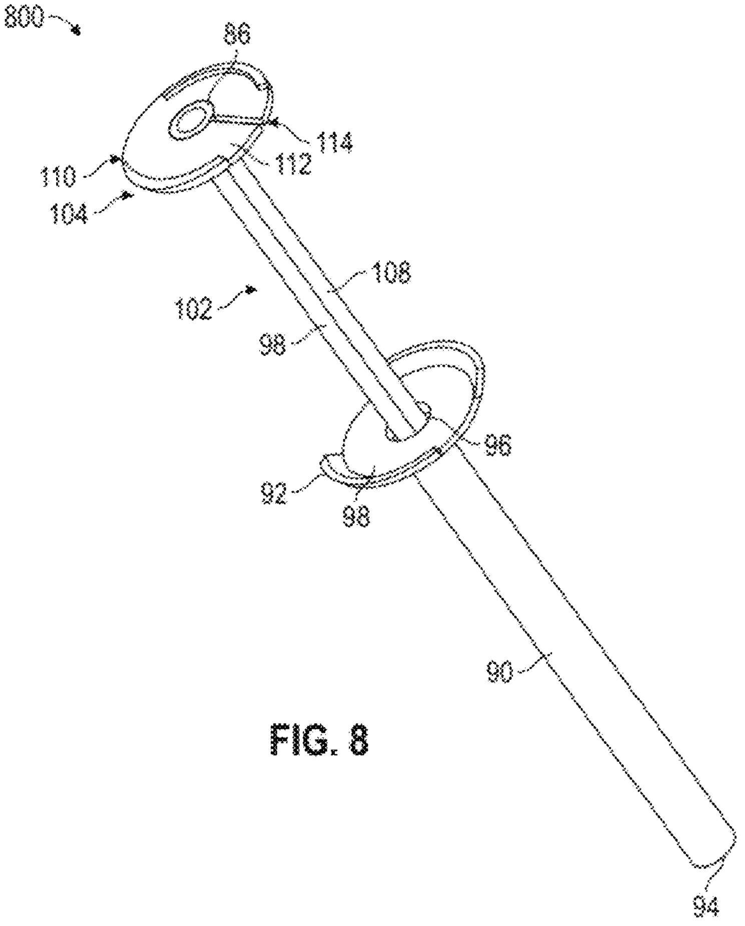
FIG. 8 illustrates a side perspective view of a surgical apparatus according to an embodiment.
Figure 9A:
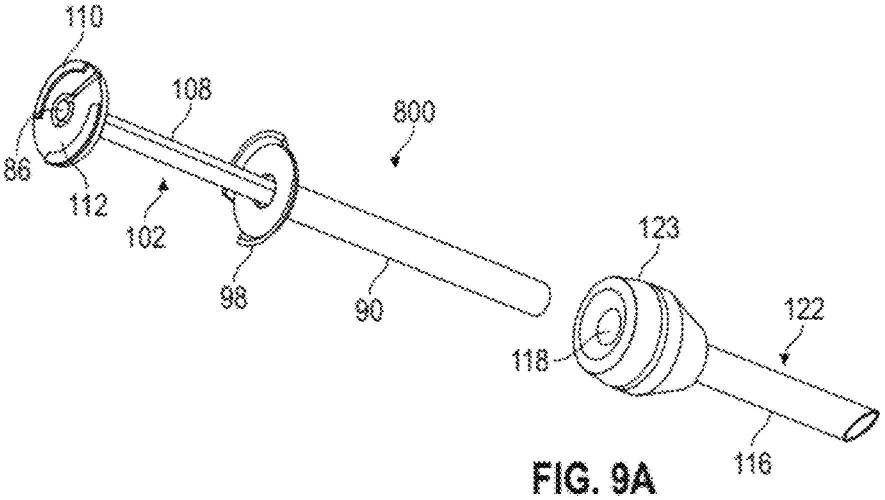
FIGS. 9A to 9G illustrate side perspective views of a surgical apparatus according to an embodiment of the invention showing the steps of inserting the surgical apparatus into a trocar through to the deployment of the protective device.
Figure 9B:
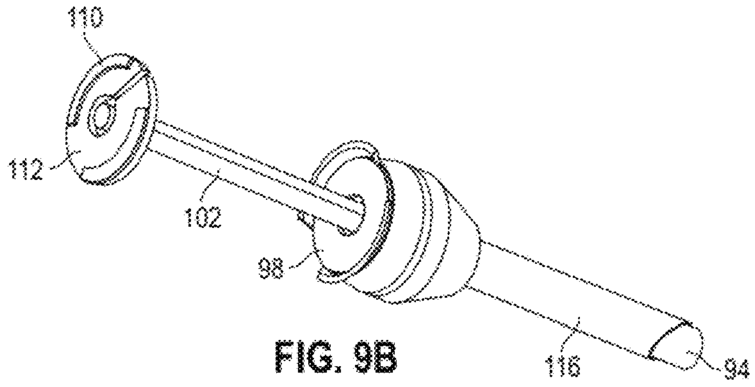
Figure 9C:
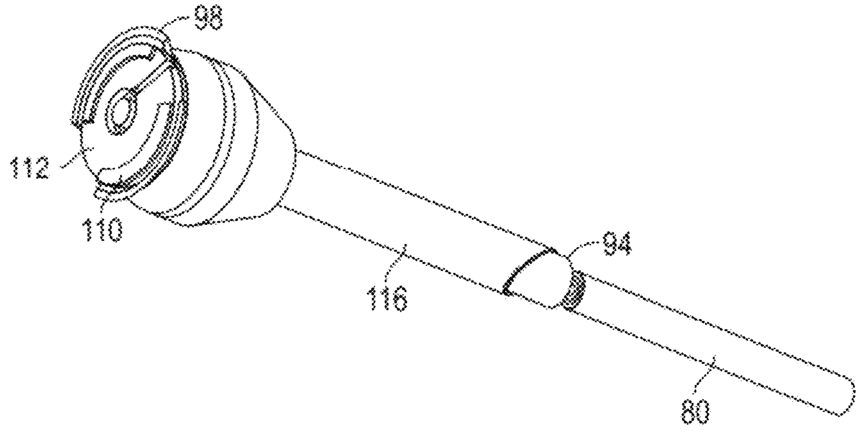
Figure 9D:
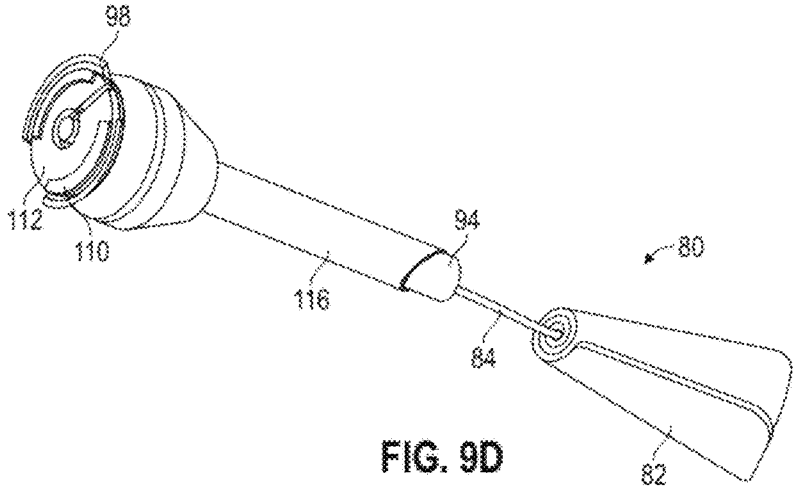
Figure 9E:
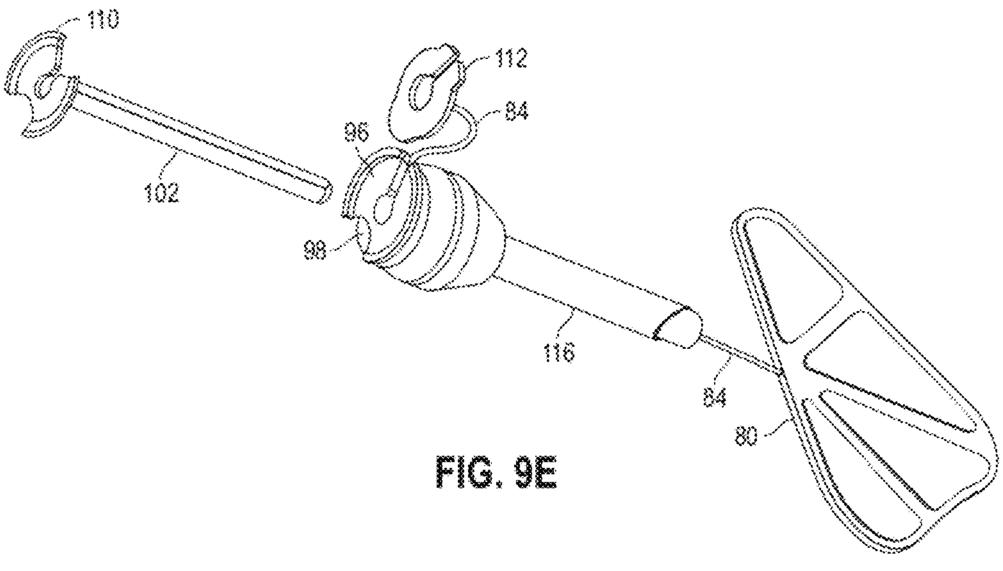
Figure 9F:
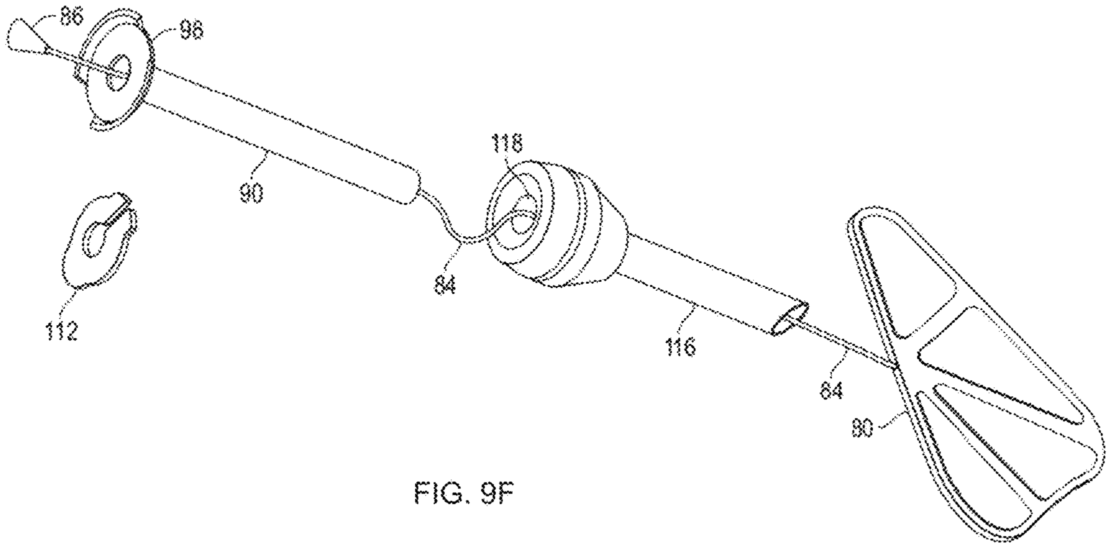
Figure 9G:
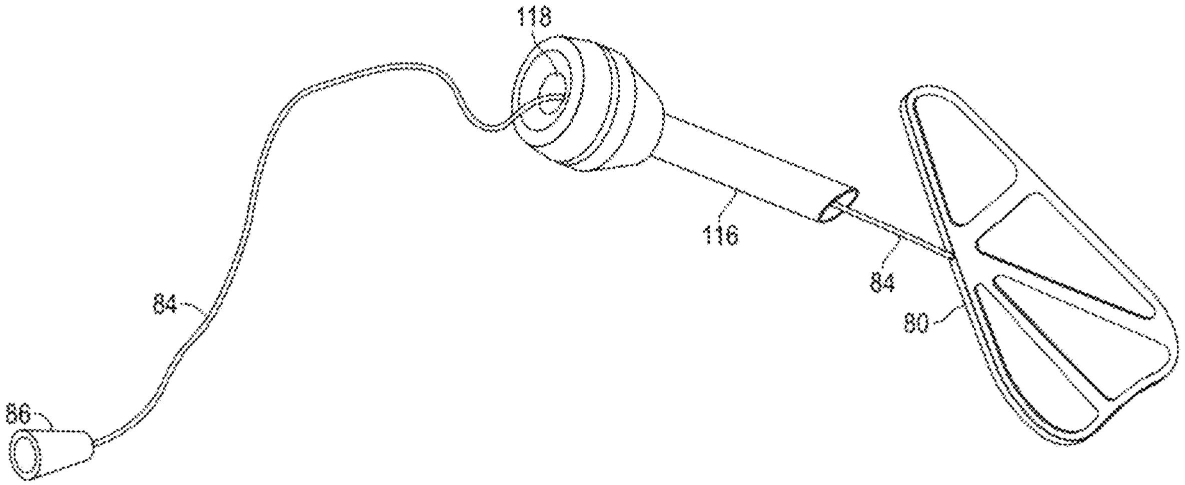
Figure 10A:
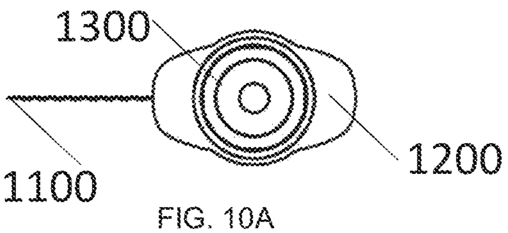
FIG. 10A is a top view of a protective assembly 1000 in accordance with an embodiment.
Figure 10B:
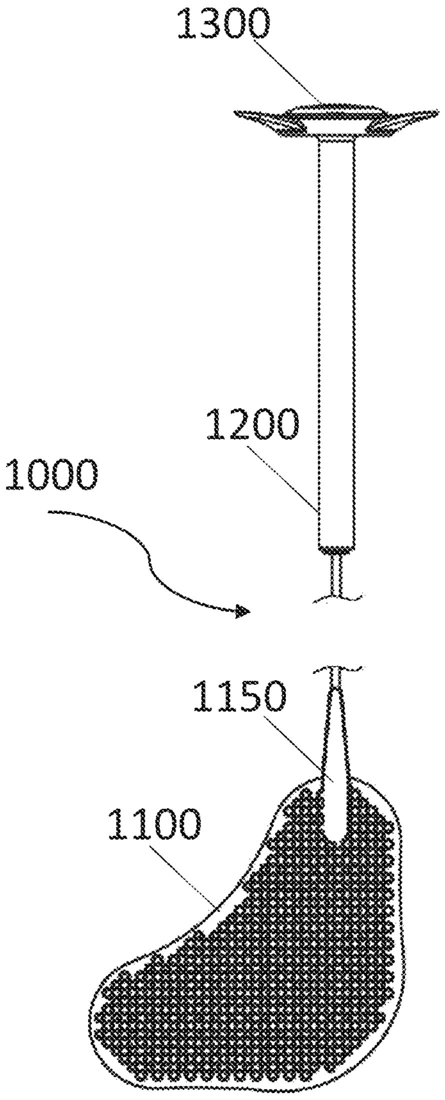
FIG. 10B is a first side view of the protective assembly 1000.
Figure 10C:
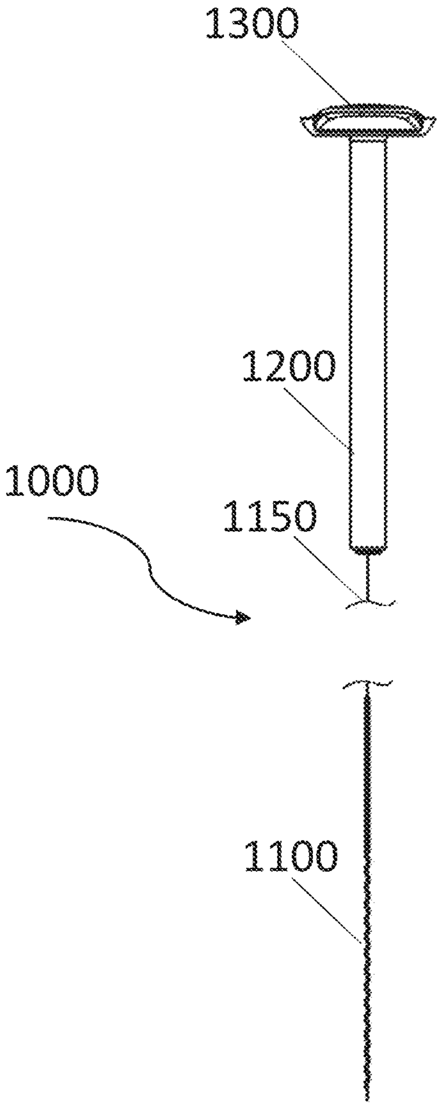
FIG. 10C is a second side view of the protective assembly 1000.
Figure 10D:
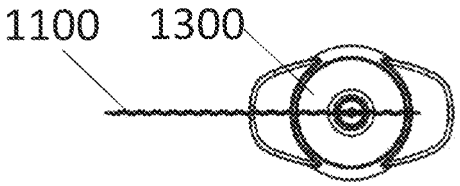
FIG. 10D is a bottom view of the protective assembly 1000.
Figures 11, 11A:
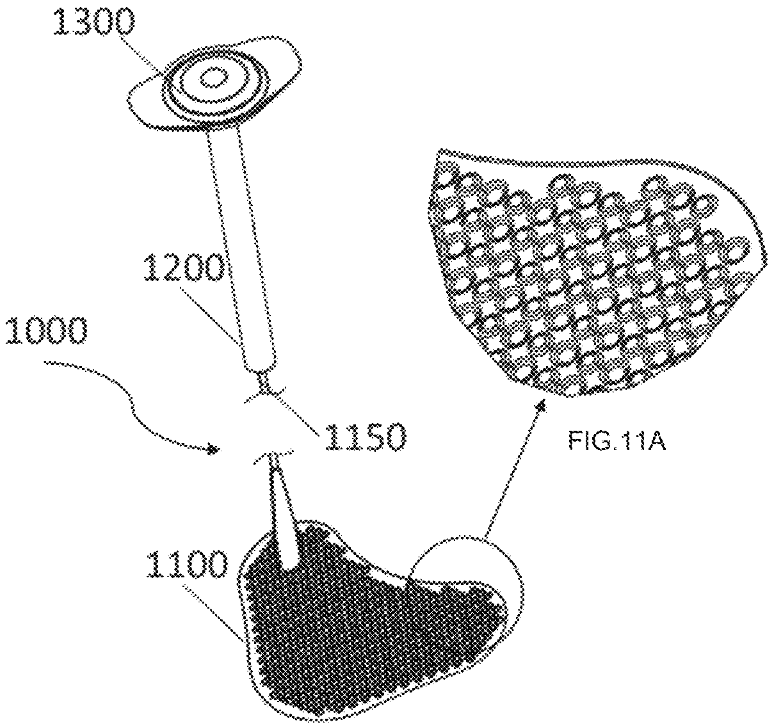
FIG. 11 is a perspective view of the protective assembly 1000.
FIG. 11A is an enlarged view of the inset shown in FIG. 11.

In FIG. 8, a surgical apparatus comprising a surgical instrument and a protective device for insertion into a patient's body is illustrated. Surgical instrument 800 comprises a housing portion 90 configured to receive a protective device therein (not shown) and a plunger 102 configured to release the protective device into a patient's body (not shown). Housing portion 90 comprises a bore (not shown) extending from a first end 92 to an opposed second end 94 and a flange 98 located at a first end 92 of the housing portion 90. Bore opening 96 of housing portion 90 is configured to receive plunger 102 therein. Plunger 102 comprises a first end 104 and an opposed second end 106, a flange 110 located at a first end 104 of plunger 102 and a recessed portion 108 extending longitudinally along the length of plunger 102. It is envisaged that in use, a retention member (not shown) of a protective device may be passed through the bore (not shown) of housing portion 90 and out bore opening 96, the retention member (not shown) may be positioned in recessed portion 108 of plunger 102 and removably secured to anchoring portion 112 via slot 114 and plug portion 86.

In FIGS. 9A to 9G, a side perspective of a surgical apparatus comprising a surgical instrument for insertion of a protective device into a patient's body is illustrated. For clarity, a patient's body is not shown, however it will be understood that a cannula 122 of a trocar may be inserted into a patient's body through an incision whilst the upper portion 123 of the trocar will remain outside the patient's body. Surgical instrument 800 comprising a housing portion 90 and plunger 102 and a protective device located within the bore of the housing portion 90 may be inserted into access port 118 of trocar 116 until flange 98 located at a first end of housing portion 90 abuts an upper surface of trocar 116. Plunger 102 is depressed until flange 110 located at a first end of plunger 102 abuts an upper surface of flange 98 of housing portion 90. As a result of the linear movement of plunger 102 in the bore (not shown) of housing portion 90, protective device 80 is released through second end 94 of housing portion 90 into a patient's body. As expandable body 82 of protective device 80 expands from an insertion condition, retention member 84 unspools into the patient's body. In use, plug portion 86 of retention member 84 and anchoring portion 112 retain the retention portion 84 in connection with surgical instrument 800.

After protective device 80 is released into a patient's body cavity, plunger 102 may be removed from the bore of housing portion 90. In use, it is envisaged that retention member 84 and anchoring portion 112 are removed from recessed portion 108 and flange 110 of plunger 102 respectively. Housing portion 90 may then be removed from access port 118 of trocar 116. In use, it is envisaged that retention member 84 is removed from slot 114 of anchoring portion 112 allowing retention member 84 to pass through the bore of housing portion 90. Retention member 84 is placed to the side so as to retain connection with protective device 80 during surgery. It is envisaged, that in use, protective device 80 may be removed from a patient's body by deflating expandable body 82 and withdrawing expandable body 82 through trocar 116. Alternatively, trocar 116 may be removed, allowing the deflated expandable body 82 to be withdrawn through the incision in the patient's body.

Referring to FIGS. 10 to 17, another preferred embodiment of a protective assembly 1000 has been illustrated. The protective assembly 1000 includes a protection member comprising a thin membrane 1100 formed from non-toxic medical grade material such as but not limited to medical grade silicone or any other type of resilient and flexible polymeric material. The protection membrane 1100 comprises an overall triangular or wing shaped configuration with rounded corners or vertices. The importance of the shape of the membrane 1100 will be described in greater detail in the foregoing sections. The thickness of the membrane 1100 is sufficiently small relative to its overall dimensions. As a result, the membrane 1100 is sufficiently thin and maneuverable to enable the membrane 1100 to be rolled into a hollow cannula of a laparoscopic trocar 1200. The membrane 1100 is configured to be unfurled or expanded and spread into a protective configuration after being passed through the cannula of the trocar 1200 once introduced within the patient's body through the trocar 1200. In such a protective configuration, the membrane 1100 may be spread over the patient's internal organs to shield the patient's organs whilst laparoscopic surgery is being carried out.

At least a peripheral portion of the membrane 1100 includes a flexible connector 1150 (of indefinite length) that connects the membrane 1100 to a distal end portion 1310 (shown in FIGS. 14 and 15) of a plunger 1300. The plunger 1300 is provided to push the membrane 1100 (in a rolled configuration) into the cannula of the trocar 1200. Specifically, one end of the flexible connector 1150 is anchored to a distal tip 1310 of the plunger and the other end of the flexible connector 1150 is fused with the matrix of the membrane 1100. The point 1152 (shown in FIG. 16) at which the flexible connector 1150 connects with the membrane 1100 is preferably reinforced or strengthened to further reduce the likelihood of the flexible connector 1150 becoming accidently uncoupled from the membrane 1100.

Figure 12A:
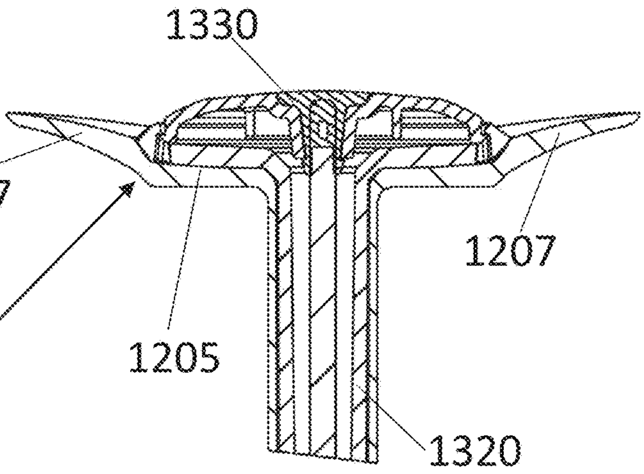
FIG. 12A is an enlarged view of the inset shown in FIG. 12.
Figure 12:
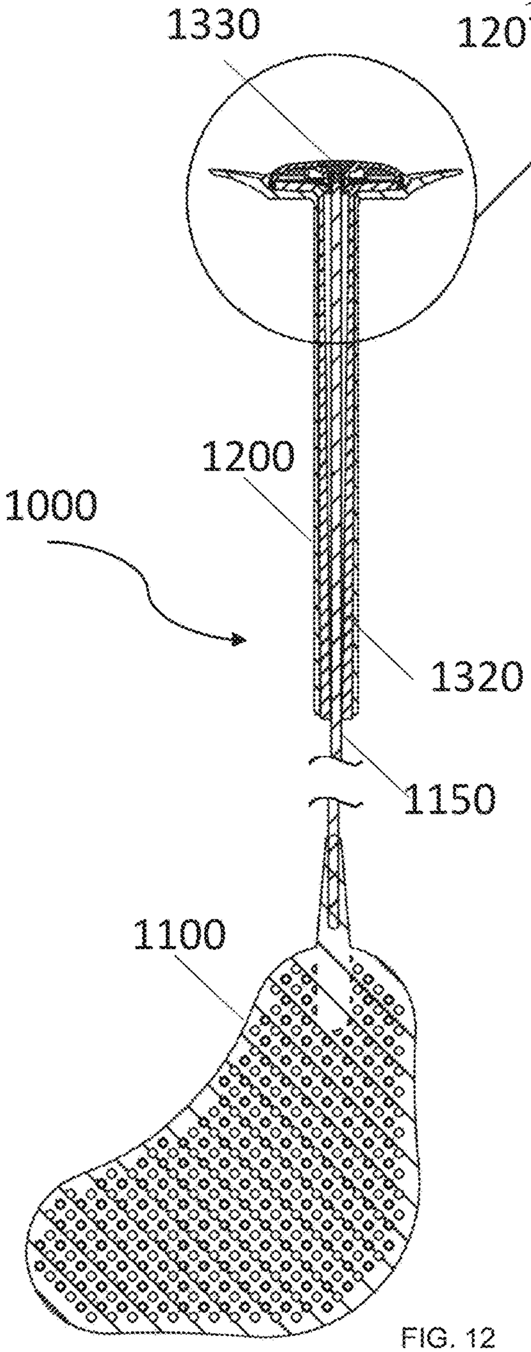
FIG. 12 is a first sectional side view of the protective assembly 1000.
Figure 13B:
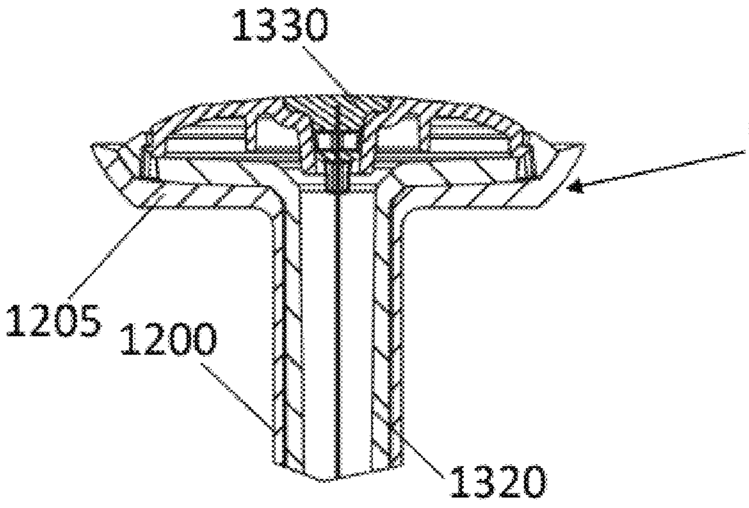
FIG. 13B is an enlarged view of a second inset shown in FIG. 13.
Figure 13A:
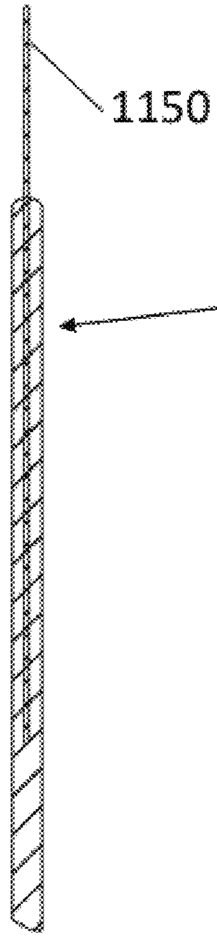
FIG. 13A is an enlarged view of a first inset shown in FIG. 13.
Figure 13:
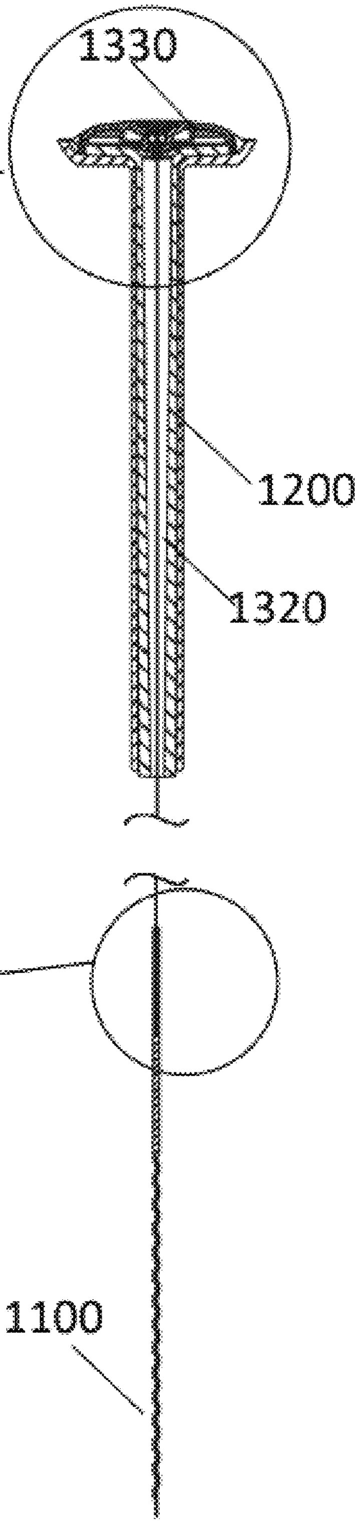
FIG. 13 is a second sectional side view of the protective assembly 1000.
Figure 14A:
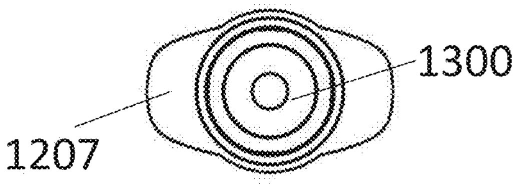
FIG. 14A is a top view of the protective assembly 1000 wherein the plunger 1300 is shown in a withdrawn position.
Figure 14B:
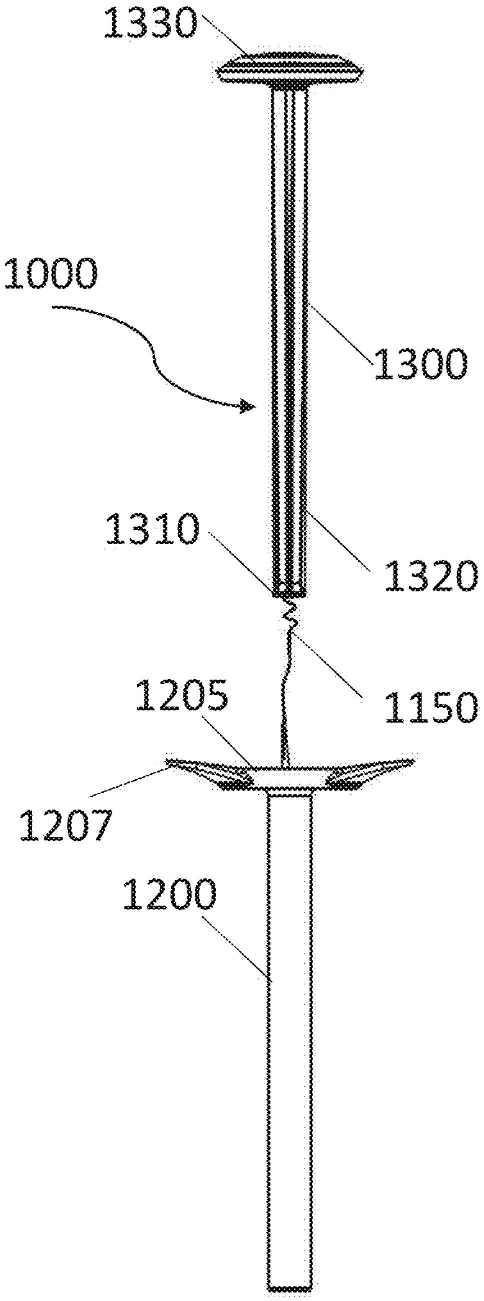
FIG. 14B is a first side view of the protective assembly 1000 wherein the plunger 1300 is shown in a withdrawn position.
Figure 14C:
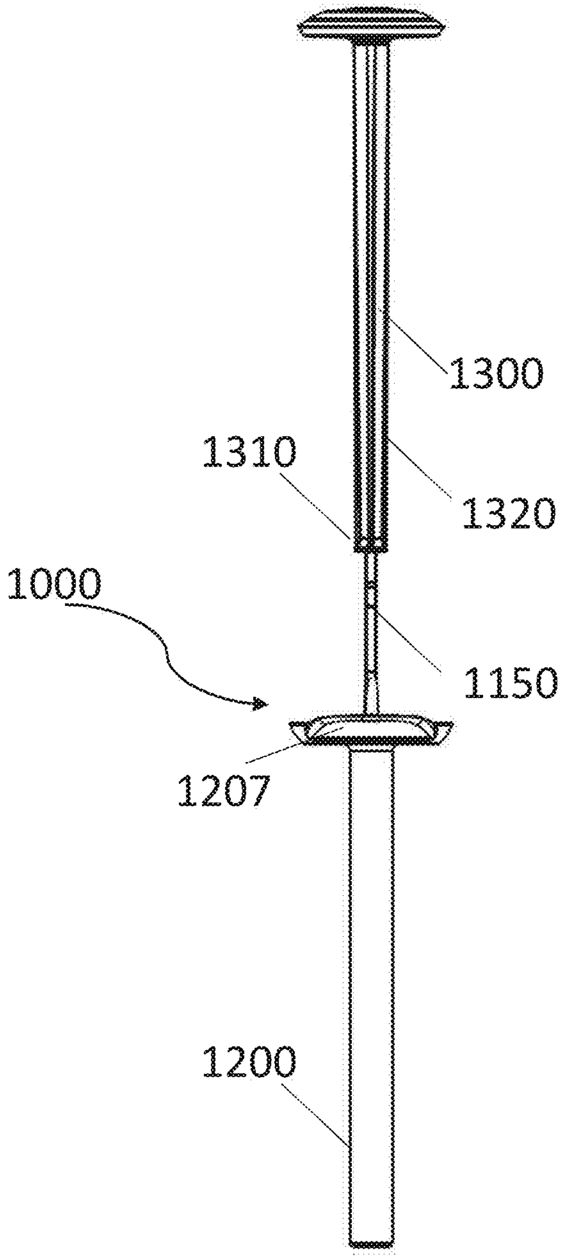
FIG. 14C is a second side view of the protective assembly 1000 wherein the plunger 1300 is shown in a withdrawn position.
Figure 14D:
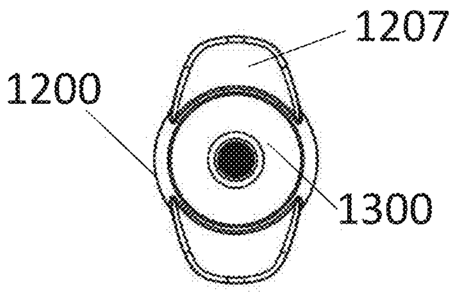
FIG. 14D is a bottom view of the protective assembly 1000 wherein the plunger 1300 is shown in a withdrawn position.
Figure 15A:
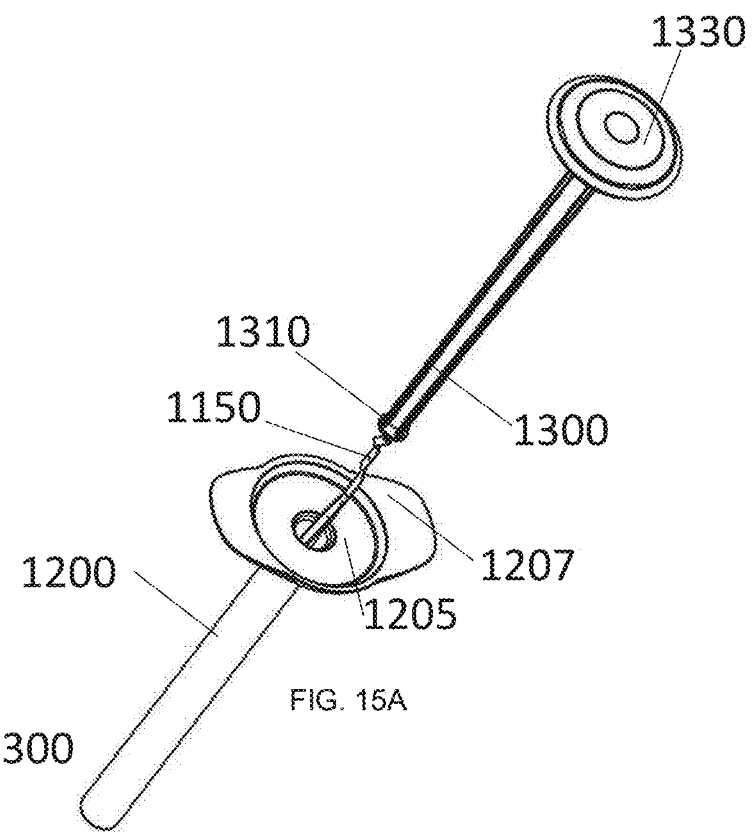
FIG. 15A is a top perspective view of the protective assembly 1000 wherein the plunger 1300 is shown in a withdrawn position.
Figure 15B:
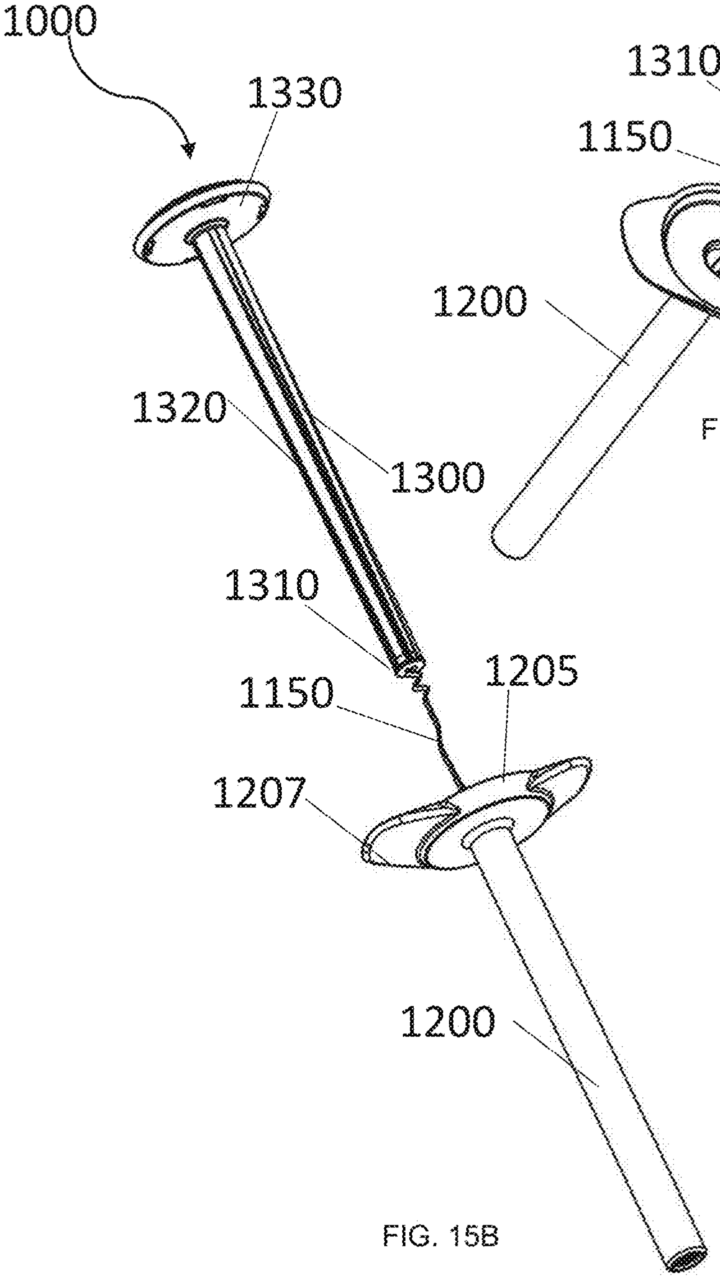
FIG. 15B is a side perspective view of the protective assembly 1000 wherein the plunger 1300 is shown in a withdrawn position.
Figure 16A:
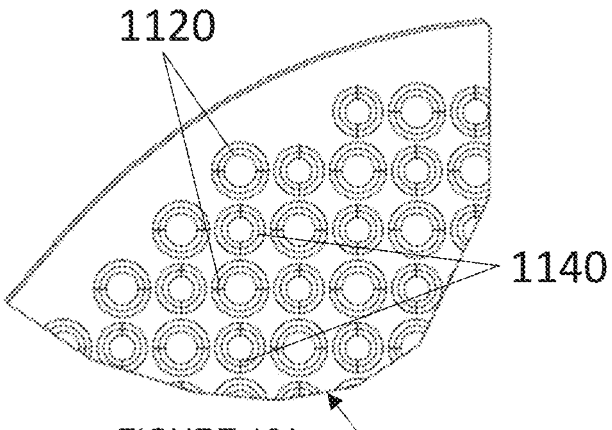
FIG. 16A is an enlarged view of the inset shown in FIG. 16.
Figure 16:
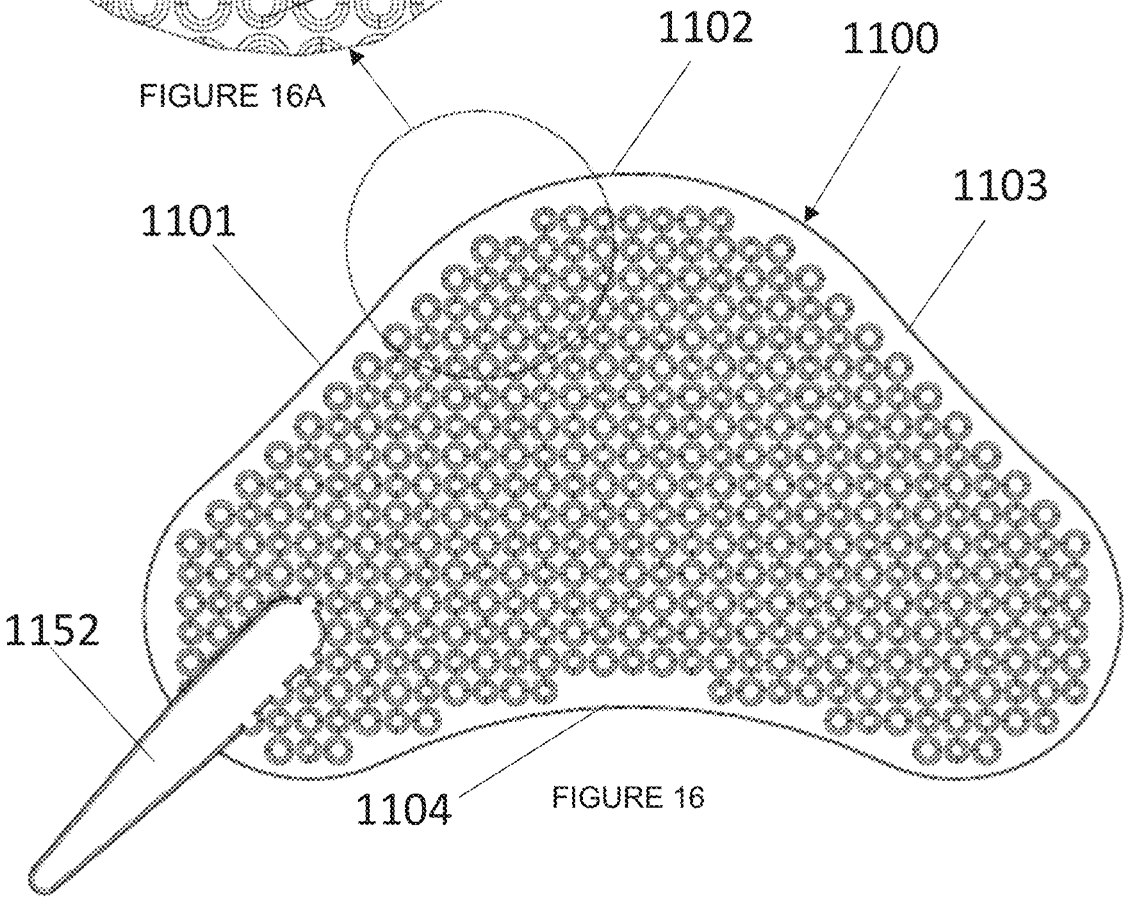
FIG. 16 is a top view (isolated) of a protection membrane 1100 which forms a part of the protective assembly 1000.
Figure 17A:
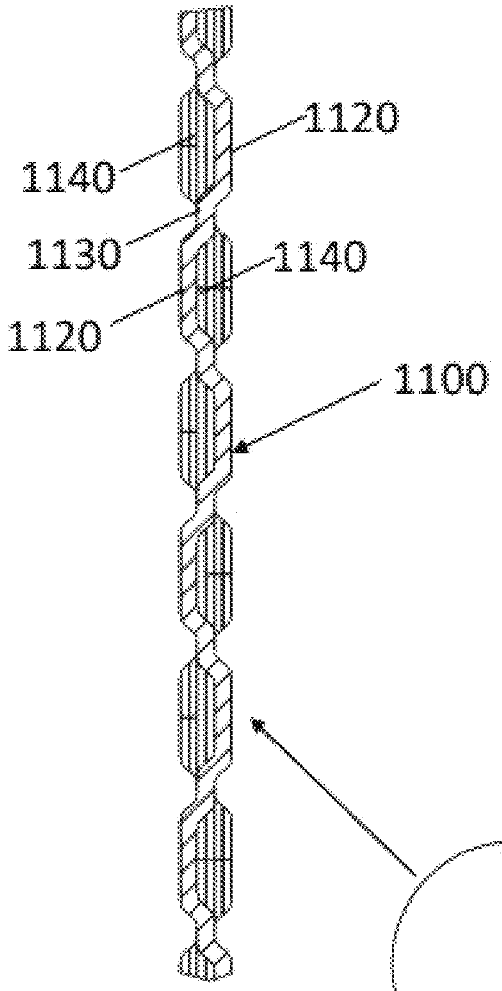
FIG. 17A is an enlarged view of the inset shown in FIG. 17.
Figure 17:
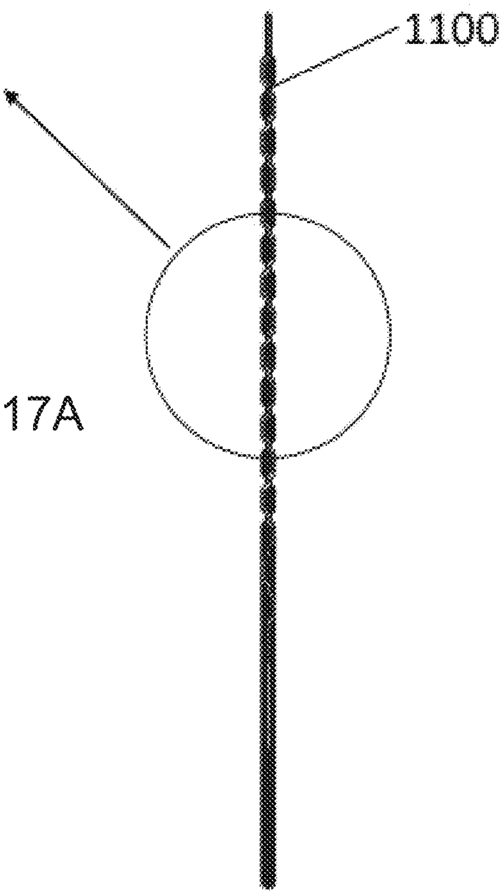
FIG. 17 is a sectional view (isolated) of the protection membrane 1100.

FIGS. 10A to 10D and FIG. 12 show the plunger 1300 in a fully inserted configuration whereby a shaft 1320 portion of the plunger 1300 has been fully inserted into the cannula of a laparoscopic trocar 1200. FIGS. 14A to 14D show the plunger 1300 in a withdrawn position (withdrawn out of the cannula of the trocar 1200). Referring to FIG. 12 in particular, the plunger 1300 includes an enlarged head 1330 that is sized to be received and seated on an entrance portion 1220 of the trocar 1200. The entrance portion of the trocar 1200 comprises a flattened flanged seat 1205 with wings or tabs 1207 extending radially from the seat 1205 so that the surgeon can place their fingers under the tabs 1207 to hold the trocar 1200. The plunger head 1330 is structured to be larger than the diameter of the cannula of the trocar 1200 to stop the plunger 1300 from falling through the cannula inside the patient's body.

The membrane 1100 comprises two major surfaces separated by a thickness of the membrane 1100. The major surfaces of the membrane 1100 comprise a substantially identical configuration with a plurality of fold regions to enable the membrane 1100 to be folded or bent (to enable rolling). Each of the major surfaces of the membrane 1100 (detailed sectional views shown in FIGS. 16 and 17). Each surface of the membrane 1100 comprises alternating rows of projections 1120 and recesses 1140 such that any two adjacently located projections 1120 are separated by a recess 1140 resulting in the said alternating configuration. Each recess 1140 on one of the major membrane surfaces of the membrane 1100 is shaped to form a trough and aligned with a projection 1140 on the other of the major membrane surfaces of the membrane 1100. It is also important to note that each of the projections 1120 or recesses 1140 on the major membrane surfaces extend in a transverse (preferably orthogonal direction) relative to a direction of the rows of the projections 1120 and recesses 1140. It is also apparent that heights for each of the projections 1120 (and depths of the recesses 1140) are substantially equal. In the preferred embodiment, the height for each projection 1120 and recesses 1140 lies in the range of 0.5 mm to 1 mm and more preferably between 0.25 mm and 0.75 mm. In at least some embodiments, the height may be 0.5 mm. Regions of the membrane 1100 form a matrix within which the projections 1120 and recesses 1140 and these membrane regions 1130 have a relatively lower thickness compared to the other regions where the projections 1120 and recesses 1140 are provided. The thickness of these regions preferably lies between 0.5 mm and 1 mm. The membrane regions with relatively lower thickness provide a plurality of fold regions along which the membrane 1100 can be easily bent (for rolling) or folded. The overall thickness of the membrane 1100 is the sum of the thickness of the these membrane regions 1130, height of the projections 1120 and depth of the recesses 1140. Therefore, if the membrane region 1130 is 0.5 mm and each of the projections have an average height of 0.5 mm and each of the recesses have an average depth of 0.5 mm, then overall thickness of the membrane 1100 would 1.5 mm.

The membrane 1100 in the preferred embodiment comprises a unique shape and provides several important advantages. Specifically, the membrane 1100, when positioned on a flat surface, comprises two linear peripheral portions 1101 and 1103 that are substantially perpendicular to each other. These two perpendicular linear portions 1101 and 1103 are bridged by a first arcuate bridging portion 1102 (with a relatively shorter arc length) and a second bridging portion 1104 (with a relatively longer arc length) which results in the membrane 1100, particularly the membrane surfaces having a wing shaped configuration.

The flexible connector 1150 may be formed from the same material as the membrane and may also be fused with the membrane 1100 as previously explained. The instantaneous width (ie. width across the connector 1150 along any section) of the flexible connector 1150 is substantially less than the overall diameter of the cannula of the trocar 1200. Such a configuration allows surgeons to use the plunger 1300 to insert the membrane 1100 (in a rolled configuration) through the cannula into the patient's body and then spreading the membrane 1100 to shield internal organs of the patient before commencing laparoscopic surgery. Whilst the surgery is being conducted, the plunger 1300 might be pulled out leaving behind a sufficient length of the flexible connector 1150 passing through the cannula of the trocar 1200. The plunger 1300 may be pulled out and placed aside whilst still being connected to the membrane 1100 by the long flexible connector 1150. Preferably, the length of the flexible connector 1150 should be much greater than the length of the cannula of the trocar to allow the membrane 1150 to be placed within the patient's body whilst the flexible connector passes through the cannula whilst still being coupled with the distal portion of the plunger 1300.

Since the flexible connector 1150 is dimensioned to be substantially small, there is enough vacant volume within the cannula of the trocar 1200 to allow insertion of other laparoscopic effectors to carry out laparoscopic surgery while the membrane 1100. Once the laparoscopic surgery has concluded, the surgeon may withdraw the membrane 1100 by pulling out the membrane through the cannula. The flexible connector 1150 is attached to a convergent peripheral portion of the membrane such that the convergent peripheral portion converges generally in a direction towards the connector to facilitate rolling or folding of the membrane 1100 when pulled into the cannula of the trocar 1200 during use. The membrane 1100 gradually broadens from a location of attachment of the connector 1150 on the membrane 1100 which results in the membrane 1100 being rolled easily into the cannula of the trocar 1200 thereby facilitating the withdrawal of the membrane 1100.

The membrane 1100 comprises 40 durometer medical grade silicone material, which is formulated for use in health care applications. The silicone base polymer used on the medical grade silicone material in the preferred embodiment of the membrane 1100 is a low volatile, peroxide free, platinum cured material that will not discolor over time. 40 durometer medical grade silicone is likely to perform well under extreme high temperatures, with capability to operate in a range of −65° C. to +232° C. The silicone material of the membrane 1100 assists with providing heat resistance to the membrane 1100. The configuration of the membrane 1100 with alternating rows of projections 1120 and recesses 1140 further improves heat insulation and allows bending and stretching of the membrane 1100 and prevents tears across the membrane 1100.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

What is claimed is:

1. A protective assembly for use during laparoscopic surgery, the assembly comprising: a thin membrane formed from non-toxic material, the membrane being sufficiently thin and maneuverable to be passed through a cannula of a trocar wherein the membrane comprises variable thickness with opposed major membrane surfaces being separated by a thickness of the membrane, wherein each surface of the opposed major membrane surfaces comprise alternating rows of fixed projections and fixed recesses, such that any two adjacently located projections are separated by a recess, wherein each recess on one of the major membrane surfaces of the membrane is shaped to form a trough and is aligned with a projection on the other of the major membrane surfaces of the membrane, wherein the any two adjacently located projections separated by a recess are configured to provide heat insulation to a tissue when the protective assembly is in a fully expanded configuration, wherein the thickness of a portion of the membrane in between the any two adjacently located projections separated by a recess is substantially less than the average height of the fixed projections and/or average depth of the fixed recesses and wherein the membrane forming the projections comprises solid sheet material.

2. A protective assembly in accordance with claim 1 wherein each of the projections on the major membrane surfaces of the membrane extend in a transverse direction relative to a direction of the rows of projections and recesses.

3. A protective assembly in accordance with claim 1, wherein average height of the projections is substantially equal to average depth of the recesses.

4. A protective assembly in accordance with claim 1, wherein the portion of the membrane in between the any two adjacently located projections separated by the recess facilitates folding or rolling of the membrane in a folded configuration.

5. A protective assembly for use during laparoscopic surgery, the assembly comprising: a thin membrane formed from non-toxic material, the membrane being sufficiently thin and maneuverable to be passed through a cannula of a trocar wherein the membrane comprises variable thickness with opposed major membrane surfaces being separated by a thickness of the membrane, wherein each surface of the opposed major membrane surfaces comprise alternating rows of fixed projections and fixed recesses, such that any two adjacently located projections are separated by a recess, wherein each recess on one of the major membrane surfaces of the membrane is shaped to form a trough and is aligned with a projection on the other of the major membrane surfaces of the membrane, wherein the any two adjacently located projections separated by a recess are configured to provide heat insulation to a tissue when the protective assembly is in use, wherein the thickness of a portion of the membrane in between the any two adjacently located projections separated by a recess is substantially less than the average height of the fixed projections and/or average depth of the fixed recesses and wherein the membrane forming the projections comprises solid sheet material, and wherein the membrane further comprises a convergent peripheral portion that converges in a direction towards a flexible connector, wherein the flexible connector extends from the membrane to facilitate rolling or folding of the membrane when pulled into the cannula of the trocar during use.

6. A protective assembly in accordance with claim 5 wherein each of the projections on the major membrane surfaces of the membrane extend in a transverse direction relative to a direction of the rows of projections and recesses.

7. A protective assembly in accordance with claim 5, wherein average height of the projections is substantially equal to average depth of the recesses.

8. A protective assembly in accordance with claim 5, wherein the portion of the membrane in between the any two adjacently located projections separated by the recess facilitates folding or rolling of the membrane in a folded configuration.

* * * * *